United States Patent [19]

Coburn et al.

[11] Patent Number: 5,747,540
[45] Date of Patent: May 5, 1998

[54] HIV PROTEASE INHIBITORS USEFUL FOR THE TREATMENT OF AIDS

[75] Inventors: Craig A. Coburn, Skippack; Randall W. Hungate, Lansdale; Richard C. A. Isaacs, Harleysville; Joseph P. Vacca, Telford; Mary Beth Young, Lansdale, all of Pa.

[73] Assignee: Merck & Co., Inc., Rahway, N.J.

[21] Appl. No.: 734,276

[22] Filed: Oct. 21, 1996

[51] Int. Cl.$^6$ ............ A61K 31/165; A61K 31/38; C07D 333/62; C07C 203/00

[52] U.S. Cl. ............ 514/622; 514/432; 514/456; 514/616; 514/374; 514/415; 514/438; 514/443; 549/53; 549/58; 549/77; 549/23; 549/404; 564/158; 564/170; 548/495; 548/238

[58] Field of Search ............ 549/53, 58, 77, 549/23, 404; 548/495, 238; 564/158, 170; 514/622, 432, 456, 616, 374, 415, 438, 443

[56] References Cited

U.S. PATENT DOCUMENTS 5,413,999  5/1995  Vacca et al. ............ 514/231.5

FOREIGN PATENT DOCUMENTS 0 541 168  5/1993  European Pat. Off.
0 609 625  10/1994  European Pat. Off.

OTHER PUBLICATIONS

Kaldor et al., "New Dipeptide Isosteres Useful for the Inhibition of HIV-1 Protease", Bioorganic & Medicinal Letters, vol. 4 (1994), pp. 1385–1390.

*Primary Examiner*—Deborah Lambkin
*Attorney, Agent, or Firm*—Melvin Winokur; Mary A. Apollina

[57] ABSTRACT

Compounds such as

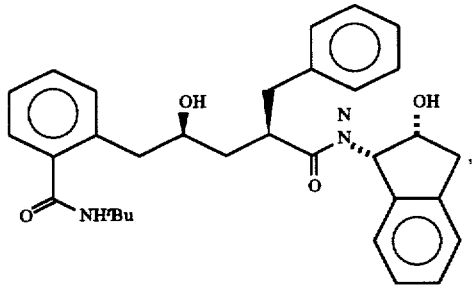

or pharmaceutically acceptable salts thereof, are HIV protease inhibitors. These compounds are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

11 Claims, No Drawings

HIV PROTEASE INHIBITORS USEFUL FOR THE TREATMENT OF AIDS

This application is related to U.S. Pat. No. 5,413,999.

The present invention is concerned with compounds which inhibit the protease encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277(1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. Applicants demonstrate that the compounds of this invention are inhibitors of HIV protease.

BRIEF DESCRIPTION OF THE INVENTION

Compounds of Formula I, as herein defined, are disclosed. These compounds are useful in the inhibition of HIV protease, the prevention of infection by HIV, the treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with compounds of Formula I, combinations thereof, or pharmaceutically acceptable salts thereof, in the inhibition of HIV protease, the prevention or treatment of infection by HIV and in the treatment of the resulting acquired immune deficiency syndrome (AIDS). Compounds of Formula I are defined as follows:

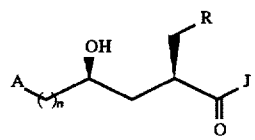

Wherein

A is
1) aryl unsubstituted or substituted with one or more of
   a) $C_{1-4}$ lower alkyl;
   b) hydroxy;
   c) halo;
   d) $C_{1-4}$ lower or branched alkoxy;
   e) $C_{1-4}$ lower branched thioalkyl;
   f) $COOR^1$;
   g) $CONHR^1$;
   h) $SO_2NHR^1$;
   i) $SO_2R^1$; or
   j) $C_{1-4}$ lower hydroxyalkyl; or
2) a 5- to 10-membered mono or bicyclic heterocycle in which one or both heterocyclic rings contain an atom selected from N, O, or S, which heterocycle is unsubstituted or substituted with one or more of
   a) $C_{1-4}$ lower alkyl;
   b) hydroxy;
   c) halo;
   d) $C_{1-4}$ lower or branched alkoxy;
   e) $C_{1-4}$ lower branched thioalkyl;
   f) $COOR^1$;
   g) $CONHR^1$;
   h) $SO_2NHR^1$;
   i) $SO_2R^1$; or
   j) $C_{1-4}$ lower hydroxyalkyl; and R is
1) aryl, unsubstituted or substituted with $C_{1-4}$ lower alkyl, $C_{1-4}$ lower alkoxy, or halo, or
2) $C_{3-7}$ cycloalkyl; and $R^1$ is $C_{1-4}$ lower alkyl, $C_{3-7}$cycloalkyl or H; and J is:

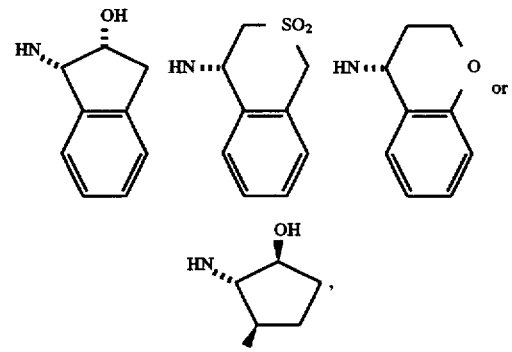

or pharmaceutically acceptable salt(s) thereof.

Within formula I, one preferred embodiment of the present invention covers compounds of the formula:

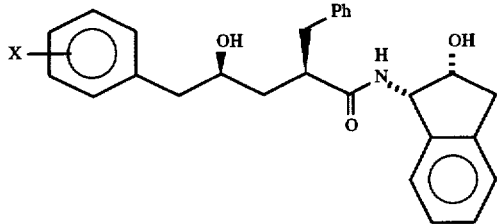

X is COOR¹; CONHR¹; SO₂NHR¹, or SO₂R¹;

or a pharmaceutically acceptable salt thereof.

Within formula I, another preferred embodiment of the present invention covers compounds of the formula:

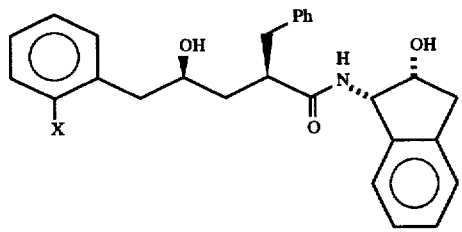

X is CONHR¹ or SO₂NHR¹, or pharmaceutically acceptable salt thereof.

Preferred compounds of the present invention include, but are not limited to:

Compound A:

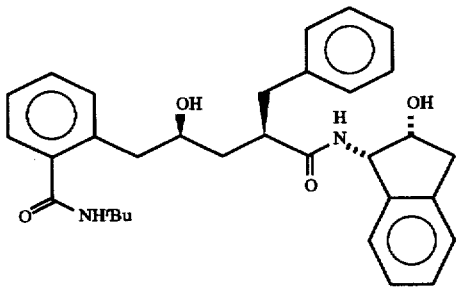

or pharmaceutically acceptable salts thereof;

Compound B:

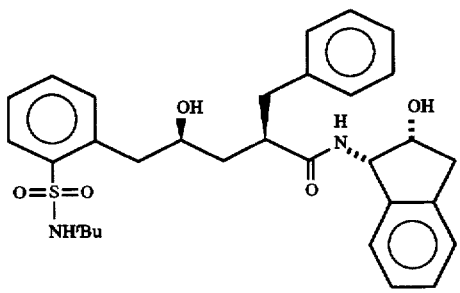

or pharmaceutically acceptable salts thereof;

Compound C:

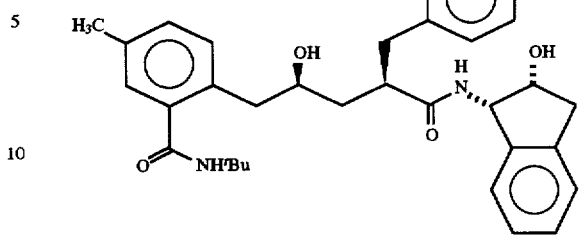

or pharmaceutically acceptable salts thereof.

The compounds of the present invention may be prepared as pharmaceutical compositions comprising any compound of the present invention and a pharmaceutically acceptable carrier. Such pharmaceutical compositions are useful in the treatment of and the delaying of the onset of AIDS, in the prevention of infection by HIV, in the treatment of infection of HIV, or in the inhibition of HIV protease. A method of treating and delaying the onset of AIDS, a method of preventing infection by HIV, a method of treating infection by HIV, and a method of inhibiting HIV protease are also disclosed. Also disclosed is a combination of compounds, which is compound A, B or C, and any of AZT (Zidovudine) or ddI or ddC.

The compounds of the present invention, may have asymmetric centers and occur as racemates, racemic mixtures and as individual diastereomers, or enantiomers with all isomeric forms being included in the present invention.

When any variable (e.g., aryl, heterocycle, R, R¹, n, etc.) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; and "cycloalkyl" is intended to include saturated ring groups, such as cyclopropyl, cyclobutyl, cyclopentyl, cyclohexyl (Cyh) and cycloheptyl. "Halo", as used herein, means fluoro, chloro, bromo and iodo; and "counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

As used herein, with exceptions as noted, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Schemes I–III for preparing the novel compounds of this invention are presented below. Tables I and II which follow the schemes illustrate the compounds that can be synthesized by Schemes I–III, but Schemes I–III are not limited by the compounds in the tables nor by any particular substituents employed in the schemes for illustrative purposes. The examples specifically illustrate the application of the following schemes to specific compounds.

Amide couplings used to form the compounds of this invention are typically performed by the carbodiimide method with reagents such as dicyclohexylcarbodiimide, or 1-ethyl-3-(3-dimethylaminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

Additional related information on synthetic background is contained in EPO 0337714.

One method for producing Formula I compounds is provided by Scheme I.

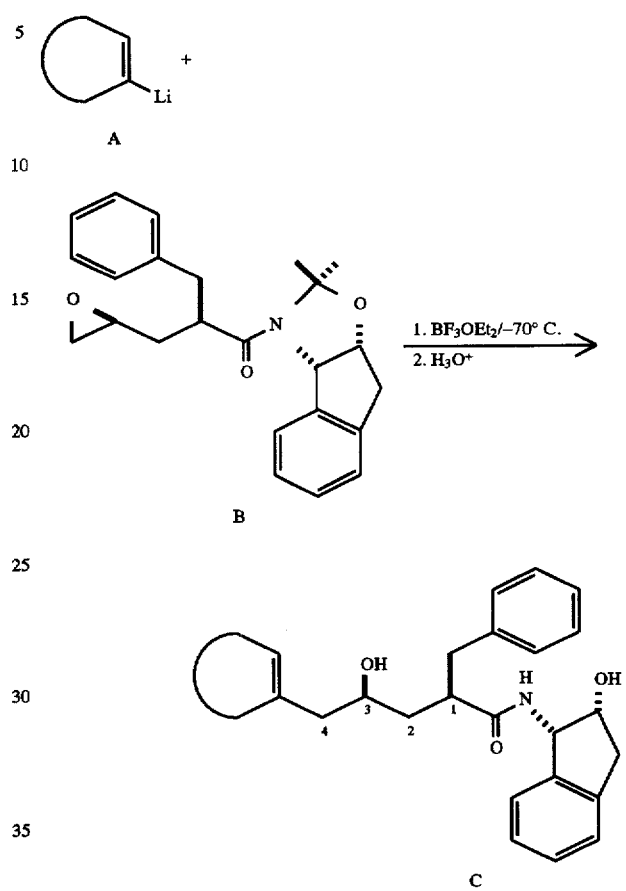

In the synthesis of the compounds of this invention, epoxide B is reacted with lithiated end group A to give an acetonide intermediate. Subsequent acid hydrolysis gives C. The reaction of epoxide with A is carried out in the presence of a mild Lewis acid such as BF$_3$. In this Scheme I, the stereochemical integrity of the carbon B is substantially retained. Epoxide B is synthesized by known procedures, e.g. Examples 1–5, U.S. Pat. No. 5,413,999, or WO 95/02583.

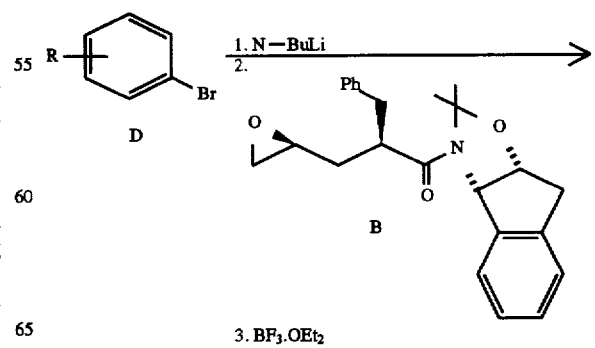

-continued
SCHEME II

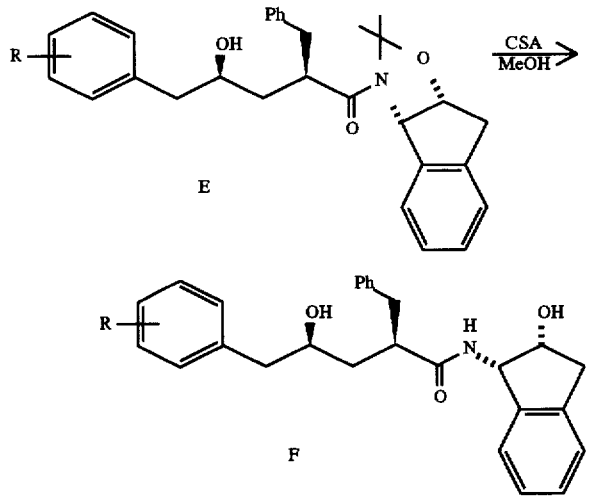

Scheme II employs a bromine derivative D as a starting material. Reaction with n-BuLi or other lithiating agents readily lithiates the end group. Subsequent reaction with epoxide B in the presence of a mild Lewis acid, followed by acid hydrolysis of the acetonide group, gives F.

useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The compounds of the present invention are useful in the inhibition of HIV protease the prevention or treatment of infection by the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

SCHEME III

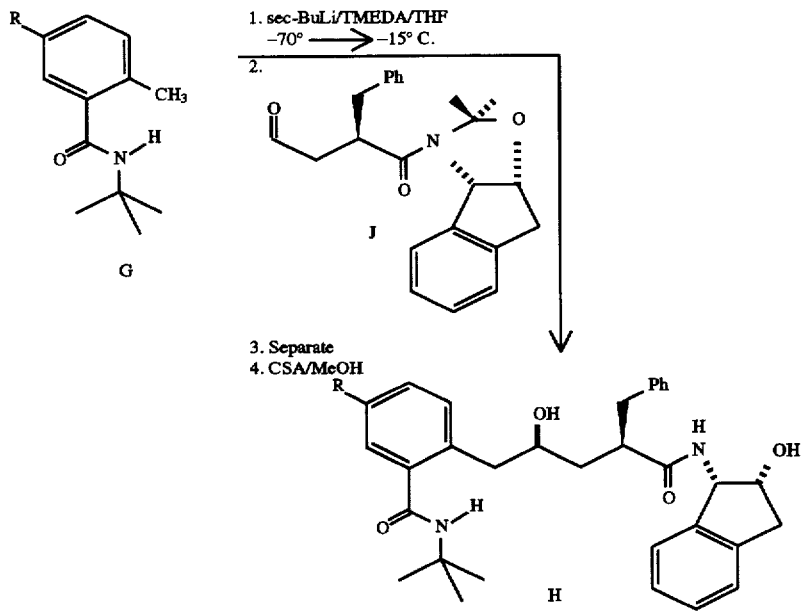

R is $C_{1-4}$ alkyl, hydroxy, halo, $C_{1-4}$ lower or branched alkoxy, $C_{1-4}$ lower branched thioalkyl, $COOR^1$, $CONHR^1$, $SO_2NHR^1$, $SO_2R^1$ or $C_{1-4}$ lower hydroxyalkyl.

In Scheme III the aldehyde J is used instead of epoxide B. Ortho-metalation of the benzamide G, followed by reaction with aldehyde J gives acetonide. Acid hydrolysis provides end product H. Aldehyde J is prepared ozonolysis of allyl acetonide of Example 1.

The compounds of this invention are useful in the preparation and execution of screening assays for antiviral compounds. For example, the compounds of this invention are Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human | Triton Biosciences | AIDS, Kaposi's |

TABLE C-continued

| Drug Name | Manufacturer | Indication |
|---|---|---|
| Interferon Beta | (Almeda, CA) | sarcoma, ARC |
| Acemannan | Carrington Labs (Irving, TX) | ARC (See also immnunomodulators) |
| Cytovene Ganciclovir | Syntex (Palo Alto, CA) | sight threatening CMV peripheral CMV retinitis |
| d4T Didehydrodeoxy thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T octapeptide Sequence | Peninsula Labs (Belmont, CA) | AIDS |
| Zidovudine; AZT AIDS, adv, ARC | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 (Rifabutin) | Adria Laboratorties (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole (Ribavirin) | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption coloumn | Advanced Biotherapy Concepts (Rockville, MD) | AIDS, ARC |
| IMMUNO-MODULATORS | | |
| AS-101 (Arsanilic acid) | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |

TABLE C-continued

| Drug Name | Manufacturer | Indication |
|---|---|---|
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS |
| HIV Core Particle Immunostimulant | Rorer (Ft. Washington, PA) | AIDS, in combination w/AZT seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK & F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis prevention of |
| Pastille Nystatin Pastille | Squibb Corp. (Princeton, NJ) | oral candidiasis |
| Ornidyl (Eflornithine Hydrochloride) | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

The synthesis of ddC, ddI and AZT (Zidovudine) are also described in EPO 484071.

Preferred combinations are simultaneous or alternating treatments of an inhibitor of HIV protease and a nucleoside inhibitor of HIV reverse transcriptase, such as AZT (Zidovudine), ddC or ddI.

Assay for Inhibition of Microbial Expressed HIV Protease

Inhibition studies of the reaction of the protease expressed in *Eschericia coli* with a peptide substrate [Val-Ser-Gln-Asn (betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 ml DMSO were added to 25 ml of the peptide solution in water. The reaction is initiated by the addition of 15 ml of 0.33 nM protease (0.11 ng) in a solution of 0.133M Na acetate pH 5.5 and 0.1% bovine serum albumin. The reaction was quenched with 160 ml of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compounds A, B and C showed $IC_{50}$ values in the range of about 1 nM-6 nM.

INHIBITION OF VIRUS SPREAD

A. Preparation of HIV-infected MT-4 cell Suspension.

MT cells were infected at Day 0 at a concentration of 250,000 per ml with a 1:1000 dilution of HIV-1 strain IIIb stock (final 125 pg p24/ml; sufficient to yield ≦1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

A matrix of nanomolar range concentrations of the pairwise combinations was prepared. At Day 1, aliquots of 125 ml of inhibitors were added to equal volumes of HIV-infected MT-4 cells (50.000 per well) in a 96-well microtiter cell culture plate. Incubation was continued for 3 days at 37° C. in 5% $CO_2$ atmosphere.

C. Measurement of Virus Spread

Using a multichannel pipettor, the settled cells were resuspended and 125 ml harvested into a separate microtiter plate. The supernatant was assayed for HIV p24 antigen.

The concentration of HIV p24 antigen was measured by an enzyme immunoassay, described as follows. Aliquots of p24 antigen to be measured were added to microwells coated with a monoclonal antibody specific for HIV core antigen. The microwells were washed at this point, and at other appropriate steps that follow. Biotinylated HIV-specific antibody was then added, followed by conjugated strepavidin-horseradish peroxidase. A color reaction occurs from the added hydrogen peroxide and tetramethylbenzidine substrate. Color intensity is proportional to the concentration of HIV p24 antigen. The $CIC_{95}$ of Compounds A and B were 800 nM and 1500 nM, respectively.

EXAMPLE 1

Conversion of Acetonide to Allyl Acetonide

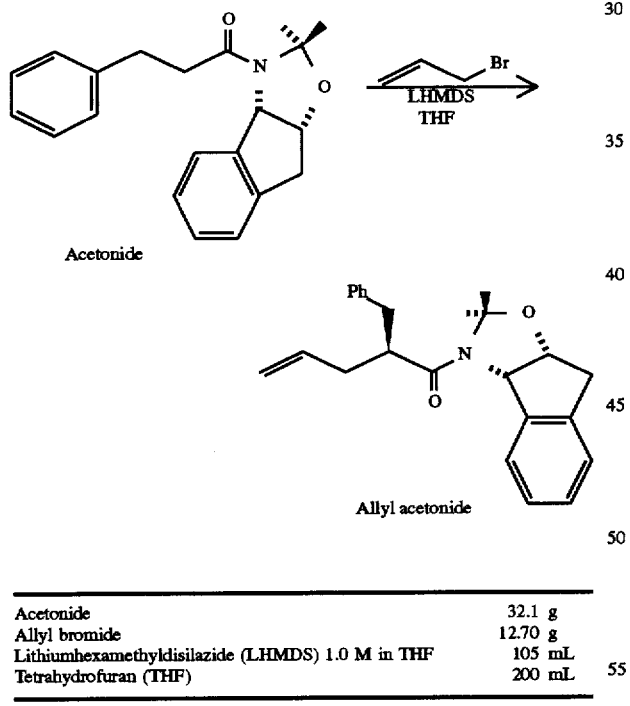

| Acetonide | 32.1 g |
| Allyl bromide | 12.70 g |
| Lithiumhexamethyldisilazide (LHMDS) 1.0 M in THF | 105 mL |
| Tetrahydrofuran (THF) | 200 mL |

The acetonide was dissolved in 200 mL THF in a 100 mL 3 neck flask equipped with an addition funnel and degassed by bubbling in nitrogen for 20 min. The mixture was cooled to −25° C. and the allyl bromide was added via a weighed syringe. The LHMDS was transferred to the addition funnel under nitrogen pressure via cannula. The LHMDS was allowed to slowly drop into the magnetically stirred reaction mixture over 20 min. The internal temperature reached −14° C. while the cooling bath was at −30° C. The mixture was aged at −20° to −15° C. for 30 min. Water (100 mL) and IPAC (100 mL) were added and the temperature rose to 5° C. The lower aqueous phase was discarded and the organic phase was washed with 100 mL of 0.2M HCl in 3% aq. NaCl, 30 mL brine, and 30 mL 0.5M sodium bicarbonate. The organic phase was evaporated (55° C., 100 Torr) to an oil, another 40 mL of IPAC were added, and the mixture was again evaporated to an oil. At this point the crude allyl acetonide may be taken directly on to the next step or purified by crystallization from 30:1 hexane-IPAC or 30:1 methylcyclohexane-IPAC to give the allyl acetonide as a white crystalline solid in 87% yield.

Allyl acetonide $^{13}C$ NMR data for major rotamer (62.5 MHz)

| 171.0 | 140.4 | 140.2 | 134.8 |
|---|---|---|---|
| 129.6 | 128.6 | 128.2 | 127.1 |
| 126.6 | 125.6 | 124.0 | 117.9 |
| 96.8 | 78.9 | | |
| | 65.6 | 47.5 | 38.6 |
| 38.0 | 36.1 | 26.6 | 24.1 ppm |

EXAMPLE 2

Conversion of Allyl Acetonide to Iodohyrin and Cyclization to Epoxide with NIS

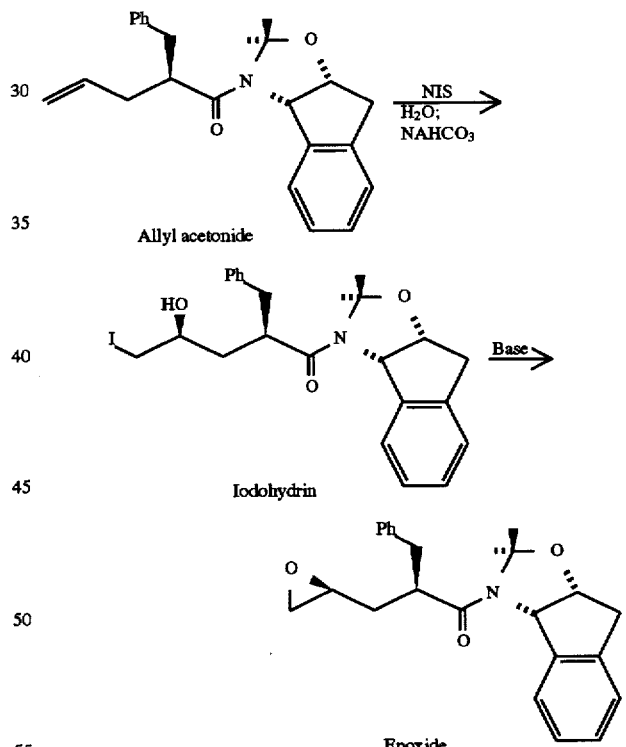

| Allyl acetonide (crude from above preparation) | ca 0.1 mol |
| N-iodosuccinimide (NIS) | 29.24 g |
| Aqueous sodium bicarbonate (0.5 M) | 350 mL |
| Isopropylacetate (IPAC) | 300 mL |

The crude allyl acetonide was dissolved in IPAC and stirred with the aqueous sodium bicarbonate and NIS for 17 h. Aqueous sodium bisulfite (38–40%) solution was added and the upper organic phase was separated. The organic phase was washed with 300 mL water and 2×100 mL brine. At this point the crude iodohydrin solution in IPAC can be directly taken on to the next step or the solution could be evaporated and crystallized from methylcyclohexane-IPAC to give the iodohydrin as a pale yellow crystalline solid. $^{13}$C NMR: m.p. rotation.

| Iodohydrin (IPAC solution crude from above preparation) | ca 0.1 ml |
| --- | --- |
| Lithium hydroxide monohydrate | 50 g |
| Water | 200 mL |

Iodohydrin $^{13}$C NMR data for major rotamer (62.5 MHz)

| | | | |
| --- | --- | --- | --- |
| 172.2 | 140.6 | 140.4 | 139.3 |
| 129.5 | 128.8 | 128.2 | 127.2 |
| 126.8 | 125.7 | 124.0 | 96.9 |
| 79.1 | 68.7 | 65.8 | 43.7 |
| 40.6 | 39.0 | 36.2 | 26.5 |
| 24.3 | 16.3 ppm | | |

EXAMPLE 3

Conversion of Allyl Acetonide to. Iodohyrin and Cyclization to Epoxide with NCS/NaI The iodohydrin in IPAC was stirred with the lithium hydroxide in water for 3 h at 25°–30° C. The upper organic phase was washed with 200 mL water and 200 mL brine and was dried over ca 2 g of magnesium sulfate. The IPAC solution was filtered and evaporated (50°–60° C., 100 Torr) down to ca 50 mL when the epoxide began to crystallize. The mixture was allowed to cool to 25° C. over 30 min and 75 mL of methylcyclohexane were added in 10 mL portions with stirring over 30 min. the mixture was aged for 1 h and the crystals were filtered off and washed with 2×20 mL methylcyclohexane and dried to give 24.10 g (64%) of the epoxide as a white crystalline solid of 99.9 A% purity by HPLC. The mother liquor and washes were evaporated to an oil and dissolved in 4 0 mL IPAC. The solution was treated with 10 g of Darco G60 carbon for 2 h at 25° C. and filtered through a pad of Solkafl°C. The filtrate was evaporated down to ca 20 mL and 40 mL of methylcyclohexane were added. The crystalline epoxide was filtered off and washed with 2×10 mL methylcyclohexane to afford another 4.96 g (13%) of epoxide 96.2 A% b HPLC. The conversion of the iodohydrin to epoxide may also be accomplished by the addition of 1.7M potassium-tert-butoxide in THF (0.70 mL, 1.2 mmol) or 5M potassium hydroxide in methanol (0.24 mL, 1.2 mmol) or DIEA (155 mg, 1.2 mmol) to a solution of the iodohydrin (505 mg, 1.0 mmol) in IPAC (2–3 mL) followed by washing with 2×2 mL water and crystallization from methylcyclohexane-IPAC.

| | |
| --- | --- |
| Allyl acetonide | 26.15 g |
| N-chlorosuccinamide (NCS) | 22.7 g |
| Sodium iodide | 25.5 g |
| Aqueous sodium bicarbonate (0.5 M) | 350 mL |
| Isopropyl acetate (IPAC) | 300 mL |

The NCS and NaI were stirred together in 200 mL of water for 20 min. The mixture turned dark brown then immediately a black solid separated out. The solid dissolved and the color faded to clear yellow with further aging. The crude allyl acetonide was dissolved in IPAC and stirred with the aqueous sodium bicarbonate and the clear yellow solution prepared above for 17 h. Aqueous sodium bisulfite (38–40%) solution was added and the upper organic phase was separated. The organic phase was washed with 300 mL water and 2×100 mL brine. At this point the crude iodohydrin solution in IPAC can be directly taken on to the next step or the solution could be evaporated and crystallized from methylcyclohexane-IPAC to give the iodohydrin as a pale yellow crystalline solid.

EXAMPLE 4

Preparation of Amide 1

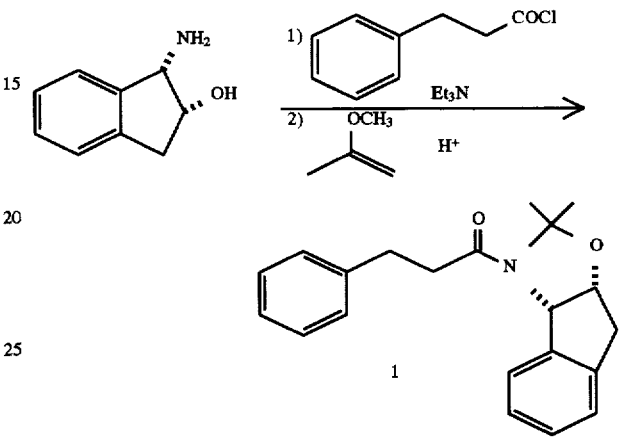

1

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500×dilution. Approximate retention times:

| retention time (min.) | identity |
| --- | --- |
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 1 (86.4%, 98 area % by HPLC). $^1$H NMR (300.13 MHz, CDCl$_3$, major rotamer) δ 7.36–7.14 (m, 9H), 5.03 (d, J=4.4, 1H), 4.66 (m, 1H) 3.15 (m, 2H), 3.06 (br s, 2H), 2.97 (m, 2H), 1.62 (s, 3H), 1.37 (s, 3H); $^{13}$C NMR (75.5 MHz, CDCl$_3$, major rotamer) dc 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1. Anal. Calcd for C$_{21}$H$_{23}$NO$_2$: C, 78.47;H, 7.21; N, 4.36. Found: C, 78.65;H, 7.24; N, 4.40.

EXAMPLE 5

Preparation of Epoxide 3
Tosylate Method

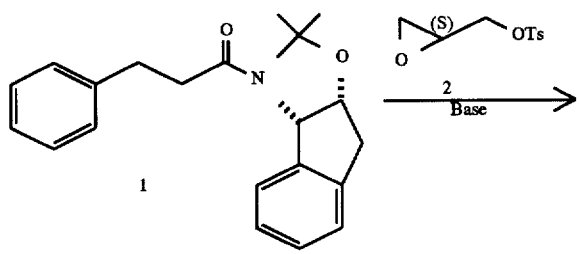

A solution of acetonide 1 (1000 g, 3.11 mol) and 2(S)-glycidyl tosylate 2 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to –56° C. Then, lithium hexamethyldisilazide (LiN[(CH$_3$)$_3$Si]2)(2.6 L, 1.38M, 1.15 equiv.) was added over 2 h, while keeping the internal temperature between –50° to –45° C. The reaction mixture was stirred at –45° to –40° C. for 1 h and then allowed to warm to –25° C. over 1 h. The mixture is stirred between –25° to –22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection= 254 nm, sample preparation=100×dilution. Approximate retention times:

| retention time (min.) | identity |
|---|---|
| 5.5 | amide 1 |
| 6.5 | glycidyl tosylate 2 |
| 13.5 | epoxide 3 |

The reaction mixture was quenched with DI water (6.7 L) at –15° C. and partitioned with ethyl acetate (10 L). The mixture was agitated and the layers were separated. The ethyl acetate extract was washed with a mixture of 1% aqueous NaHCO$_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 3 (61.2%, 98.7 area % of the major epoxide by HPLC): $^{13}$C NMR (300 MHz, CDCl$_3$) δ 171.1, 140.6, 140.5, 139.6, 129.6, 128.8, 128.2, 127.2, 126.3, 125.6, 124.1, 96.8, 79.2, 65.8, 50.0, 48.0, 44.8, 39.2, 37.4, 36.2, 26.6, 24.1.

EXAMPLE 6

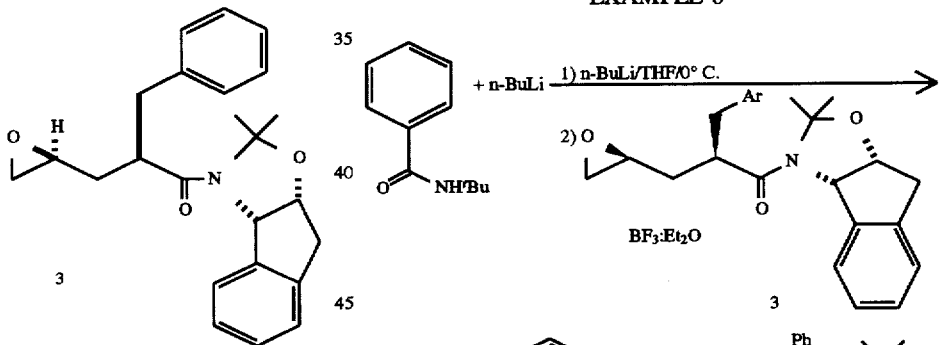

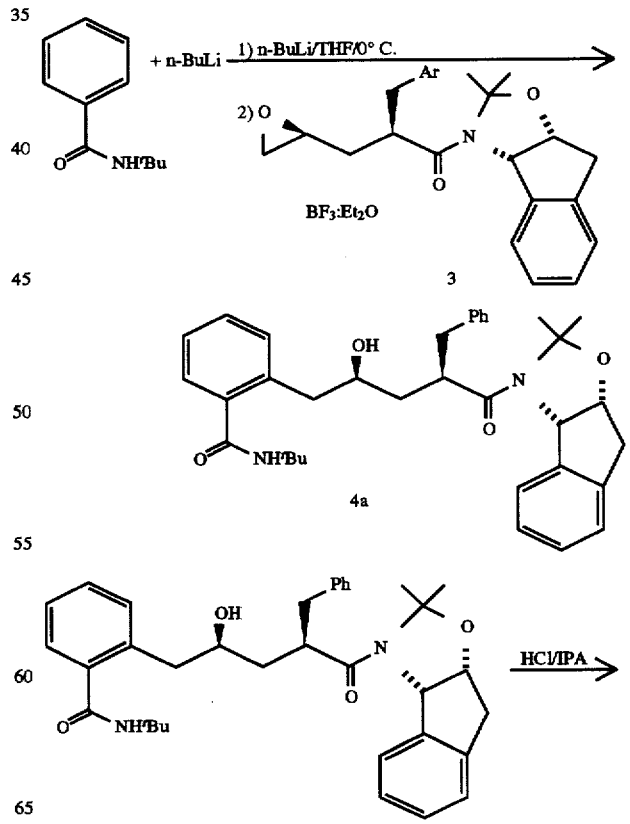

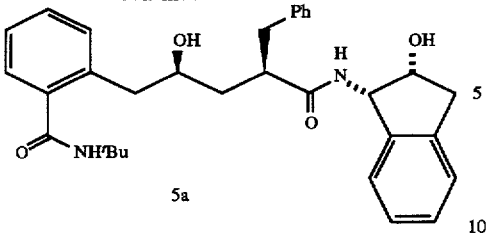

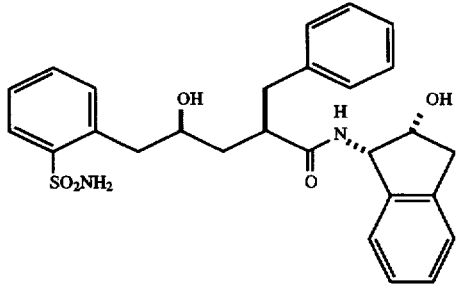

To a 0° C. solution of N-tert-butylbenzamide (531 mg, 3.0 mmol) in 10 mL of THF was added 2.44 mL (6.1 mmol) of n-BuLi (2.5M in hexanes). The yellow solution was stirred at this temperature for 2 h before cooling to −70° C. The resulting dianion was then treated with epoxide 3 (377.5 mg, 1.0 mmol) in 2 mL of THF followed immediately with 0.37 mL (3.1 mmoL) of BF₃OEt₂. The reaction mixture was stirred for 40 min and quenched with 5 mL of sat'd NaHCO₃ and diluted with 5 mL of Et₂O. The aqueous phase was extracted with 3×5 mL of Et₂O. The combined organic extracts were washed with brine and dried over MgSO₄. The yellow oil was subjected to flash chromatography (SiO₂; gradient 1:4, 1:3, 1:1 EtOAc/Hex) to afford compound 4a.

The above acetonide (49.1 mg, 0.0885 mmol) was dissolved in 1 mL of 2-propanol and cooled to 0° C. The solution was treated with 0.27 mL of 8N HCl and was allowed to stir to ambient temperature over 4 h. The pH of the solution was then adjusted to 12 by the dropwise addition of 50% NaOH at 0° C. The aqueous solution was extracted with 3×5 mL portions of CH₂Cl₂ and the combined organic extracts were washed with brine (2×5 mL) and dried (MgSO₄). Column chromatography (7:3 EtOAc/Hex) afforded 45.4 mg (92%) of 5a as a white solid.

¹H NMR (CDCl₃) δ1.47 (s, 9H), 1.76 (t, J=11.2 Hz, 1H), 2.10 (t, J=10.4 Hz, 1H), 2.70–3.01 (m, 5H), 3.93 (bs, 1H), 4.26 (bs, 1H), 5.29 (dd, J=5.1, 6.9 Hz, 1H), 5.45 (d, J=4.9 Hz, 1H), 5.96 (d, J=8.1 Hz, 1H), 5.98 (s, 1H), 7.0–7.4 (m, 13H). MS (FAB) M+1=515.

Anal calc'd for C₃₂H₃₈N₂O₄·0.8 H₂O: C, 72.64; H, 7.54; N, 5.30. Found: C, 72.62; H, 7.68; N, 5.09.

EXAMPLE 7

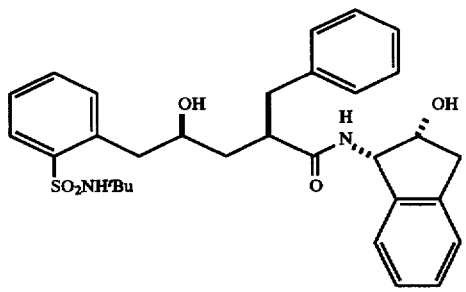

A −70° C. solution of N-(tert-butyl) benzene sulfonamide (639 mg, 3.0 mmol) in 10 mL of THF was treated with 2.44 mL (6.1 mmol) of n-BuLi (2.5M in hexanes). The yellow solution was stirred at this temperature for 10 min then 0° C. for 90 min. The solution was recooled to −70° C. and epoxide 3 (377.5 mg, 1.0 mmol) in 3 mL of THF was added followed by the addition of 0.37 mL (3.1 mmoL) of BF₃OEt₂. The reaction mixture was stirred for 1 h and quenched with 2 mL of sat'd NaHCO₃ and diluted with 5 mL of Et₂O. The aqueous phase was extracted with 3×5 mL of EtOAc. The combined organic extracts were washed with brine and dried over MgSO₄. The yellow oil was subjected to flash chromatography (SiO₂; gradient 4:1, 1:1 EtOAc/Hex) to afford 224 mg (38%) of 4b.

Acetonide 4b (121 mg, 0.205 mmol) was dissolved in 2 mL of 2-propanol and 4 mL of THF and cooled to 0° C. The solution was treated with 0.64 mL of 8N HCl and was allowed to stir to ambient temperature over 4.5 h. The solution was neutralized by the dropwise addition of 50% NaOH at 0° C. The aqueous solution was extracted with 3×5 mL portions of EtOAc and the combined organic extracts were washed with brine (2×5 mL) and dried (MgSO₄). Column chromatography (7:3 EtOAc/Hex) afforded 28 mg (25%) of 5b mp=185°–187° C. and 25 mg (25%) of 6b as a white solid; mp=194°–197° C.

Compound 5b

¹H NMR (CDCl3) δ1.33 (s, 9H), 1.66 (t, J=11.2 Hz, 1H), 2.05 (t, J=10.4 Hz, 1H), 2.80–3.10 (m, 5H), 3.35 (dd, J=2, 14 Hz, 1H), 3.60 (m, 2H), 3.98 (bs, 1H), 4.26 (bq, J=4.6 Hz, 1H), 5.32 (dd, J=4.5, 8.2 Hz, 1H), 5.96 (d, J=8.2 Hz, 1H), 7.05–7.60 (m, 12H), 7.90 (d, J=7.5 Hz, 1H). MS (FAB) M+1=551.

Anal calc'd for C₃₁H₃₈N₂SO₅·0.05 H₂O: C, 67.49; H, 6.96, N, 5.08. Found: C, 67.11; H, 6.91; N, 5.09.

Compound 6b

¹H NMR (CDCl₃) δ1.66 (t, J=11.2 Hz, 1H), 1.85 (t, J=10.4 Hz, 1H), 2.85–3.10 (m, 5), 3.85 (bs, 2H), 4.26 (bq, J=4.6 Hz, 1H), 5.18 (t, J=8 Hz, 1H), 5.21 (dd, J=4.5, 8.2 Hz, 1H), 6.00 (d, J=8.2 Hz, 1H), 7.05–7.60 (m, 12H), 7.80 (d, J=7.5 Hz, 1H). MS (FAB) M+1=495.

Anal calc'd for C₂₇H₃₀N₂SO₅·0.3 CHCl₃: C, 61.81; H, 5.76, N, 5.22. Found: C, 61.55; H, 5.90; N, 5.24.

EXAMPLE 8

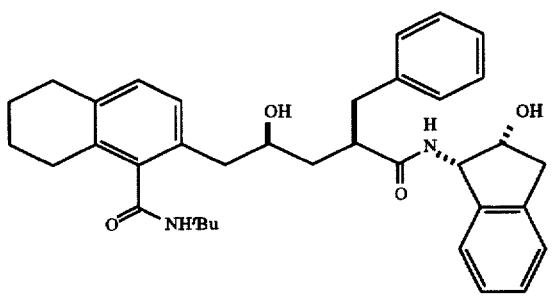

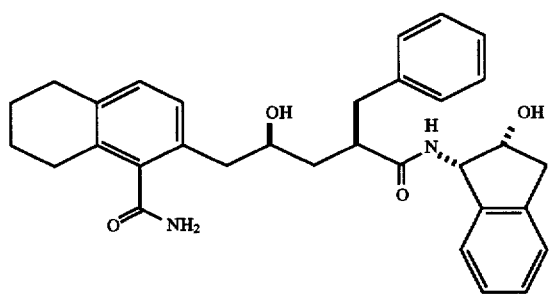

A 0° C. solution of N-(tert-butyl)-1-naphthalenamide (681 mg, 3.0 mmol) in 10 mL of THF was treated with 2.44 mL (6.1 mmol) of n-BuLi (2.5M in hexanes). The red solution was stirred at this temperature for 100 min, cooled to −70° C. and treated with epoxide 3 (377.5 mg, 1.0 mmol) in 3 mL of THF. After 1 min, 0.37 mL (3.1 mmoL) of $BF_3OEt_2$ was added. The reaction mixture was stirred for 1 h and quenched with 2 mL of sat'd $NaHCO_3$ and diluted with 5 mL of $Et_2O$. The aqueous phase was extracted with 3×5 mL of EtOAc. The combined organic extracts were washed with brine and dried over $MgSO_4$. The yellow oil was subjected to flash chromatography ($SiO_2$; 1:1 EtOAc/Hex) to afford 289 mg (48%) of 4c.

Acetonide 4c (168.3 mg, 0.278 mmol) was dissolved in 6 mL of methanol and treated with 179 mg (0.771 mmol) of CSA and was allowed to stir to ambient temperature over 3 h. The solution was rotovaped and the residue was dissolved in EtOAc and extracted with 3×5 mL portions of $NaHCO_3$. The organic phase was washed with brine (2× 5 mL) and dried ($MgSO_4$). Column chromatography (1:1 EtOAc/Hex) afforded 101 mg (64%) of 5c as a mixture of rotomers mp=111°–121° C.

$^1$H NMR ($CDCl_3$) δ 1.46 and 1.61 (each s, 9H), 1.76 (m, 2H), 2.40–3.30 (m, 5H), 3.83 (bs, 1H), 4.18 (d, J=4.4 Hz, 1H), 4.20 (d, J=3.7 Hz, 1H), 5.25 (m, 1H), 5.84 (d, J=7.9 Hz, 1H), 5.94 (d, J=7.1 Hz, 1H), 7.0–8.0 (m, 15H). MS (FAB) M+1=565.

Anal calc'd for $C_{36}H_{40}N_2O_4 \cdot 1.1\ H_2O$: C, 73.96; H, 7.28, N, 4.79. Found: C, 73.66; H, 6.98; N, 4.75.

Acetonide 4c (200 mg, 0.33 mmol) was dissolved in 4 mL of 2-propanol and 2 mL of THF and cooled to 0° C. The solution was treated with 1.2 mL of 8N HCl and was allowed to stir to ambient temperature over 4.5 h. The solution was basified (pH=11) by the dropwise addition of 50% NaOH at 0° C. The aqueous solution was extracted with 3×5 mL portions of EtOAc and the combined organic extracts were washed with brine (2×5 mL) and dried ($MgSO_4$). Column chromatography (1:1 EtOAc/Hex) afforded 149 mg (89%) of 6c as a white solid; mp=220°–222° C.

$^1$H NMR (5% DMSO-$d_6$/$CDCl_3$) δ 1.73 (t, J=10.4 Hz, 1H), 2.10 (t, J=10.4 Hz, 1H), 2.80–3.05 (m, 5H), 3.44 (m, 1H), 3.80 (m, 1H), 4.00 (bs, 1H), 4.28 (bs, 1H), 4.85 (d, J=4.1 Hz, 1H), 5.32 (dd, J=5.1, 8.3 Hz, 1H), 7.0–8.3 (m, 15H).

Anal calc'd for $C_{32}H_{32}N_2O_4 \cdot 0.25\ H_2O$: C, 71.93; H, 6.04, N, 5.20. Found: C, 71.68; H, 6.15; N, 5.33.

EXAMPLE 9

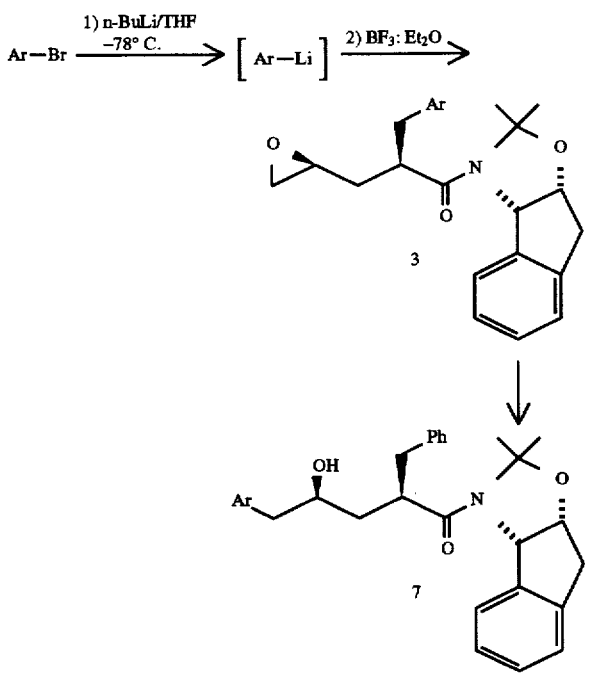

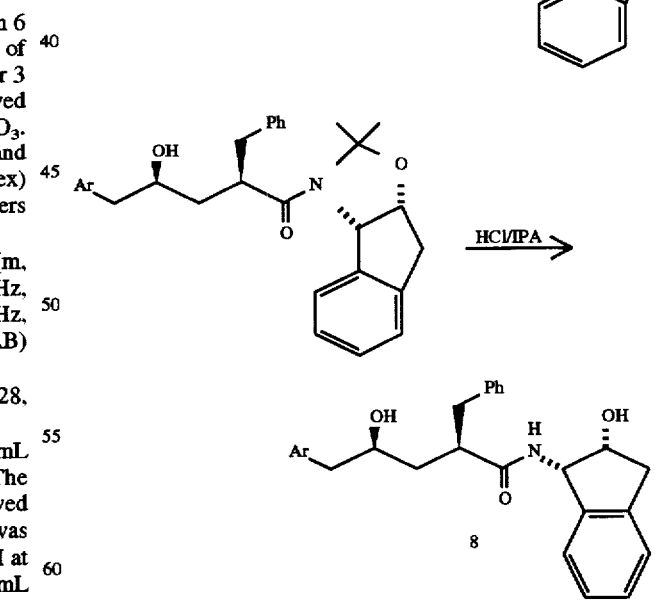

A. Compound 8a

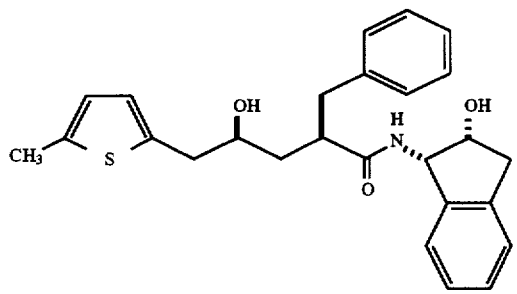

To a 0° C. solution of 2-methylthiophene (0.14 mL, 1.5 mmol) in 7 mL of Et$_2$O was added 0.60 mL (1.5 mmol) of n-BuLi (2.5M in hexanes). The yellow solution was stirred at this temperature for 2 h before cooling to −70° C. The resulting anion was then treated with epoxide 3 (188 mg, 0.50 mmol) in 2 mL of THF followed immediately with 0.18 mL (1.5 mmoL) of BF$_3$OEt$_2$. The reaction mixture was stirred for 30 min and quenched with 5 mL of sat'd NaHCO$_3$ and diluted with 5 mL of Et$_2$O. The aqueous phase was extracted with 3×5 mL of Et$_2$O. The combined organic extracts were washed with brine and dried over MgSO$_4$. The yellow oil was subjected to flash chromatography (SiO$_2$; 1:1 EtOAc/Hex) to afford 160 mg (68%) of acetonide 7a.

The above acetonide (47.5 mg, 0.10 mmol) in 6 mL of methanol was treated with 232 mg (1.0 mmol) of camphorsulfonic acid and the whole was stirred for 4 h. The solvent was removed with reduced pressure and the residue was taken up in 10 mL of EtOAc and was washed with sat'd NaHCO$_3$ (3×2 mL). The organic extracts were washed with brine (2×2 mL) and dried (MgSO$_4$). Column chromatography (gradient; 2:1, 1:1 EtOAc/Hex) afforded 35 mg (80%) of 8a as a white solid.

$^1$H NMR (CDCl$_3$) δ 1.76 (t, J=11.2 Hz, 1H), 2.08 (t, J=10.4 Hz, 1H), 2.41 (s, 3H), 2.70–3.01 (m, 5H), 3.98 (bs, 1H), 4.22 (bs, 1H), 5.25 (m, 1H), 5.80 (d, J=8.1 Hz, 1H), 6.60 (s, 1H), 6.64 (s, 1H), 7.0–7.4 (m, 9 H).

Anal calc'd for C$_{26}$H$_{29}$NSO$_3$0.25 H$_2$O: C, 70.95; H, 6.76, N, 3.18. Found: C, 70.98; H, 6.54; N, 3.31.

B. Compound 8b

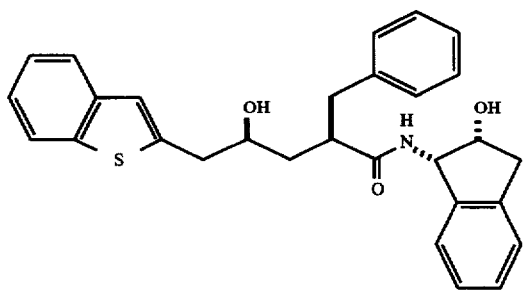

To a 0° C. solution of thianaphthalene (402 mg, 3.0 mmol) in 10 mL of Et$_2$O was added 1.2 mL (3.0 mmol) of n-BuLi (2.5M in hexanes). The yellow solution was stirred at this temperature for 2 h before cooling to −70° C. The resulting anion was then treated with epoxide 3 (377.5 mg, 1.0 mmol) in 5 mL of THF followed immediately with 0.37 mL (3.0 mmoL) of BF$_3$OEt$_2$. The reaction mixture was stirred for 30 min and quenched with 5 mL of sat'd NaHCO$_3$ and diluted with 5 mL of Et$_2$O. The aqueous phase was extracted with 3×5 mL of Et$_2$O. The combined organic extracts were washed with brine and dried over MgSO$_4$. The yellow oil was hydrolysed directly without further purification.

The above acetonide (102 mg, 0.20 mmol) in 12 mL of methanol was treated with 232 mg (1.0 mmol) of camphor-sulfonic acid and the whole was stirred for 4.1 h. The solvent was removed with reduced pressure and the residue was taken up in 10 mL of EtOAc and was washed with sat'd NaHCO$_3$ (3×2 mL). The organic extracts were washed with brine (2×2 mL) and dried (MgSO$_4$). Column chromatography (1:2, EtOAc/Hex) afforded 75 mg (79%) of 8b as a white solid; mp=166°–168° C.).

$^1$H NMR (CDCl$_3$) δ 1.76 (t, J=11.2 Hz, 1H), 2.11 (t, J=10.4 Hz, 1H), 2.44 (s, 1H), 2.78–3.20 (m, 5H), 4.08 (bs, 1H), 4.12 (bs, 1H), 5.25 (m, 1H), 5.77 (d, J=8.1 Hz, 1H), 7.0–7.4 (m, 12H), 7.72 (d, J=8 Hz, 1H), 7.80 (d, J=8Hz, 1H).

Anal calc'd for C$_{29}$H$_{29}$NSO$_3$: C, 73.86; H, 6.20, N, 2.97. Found: C, 73.72 H, 6.21; N, 3.15.

C. Compound 8c

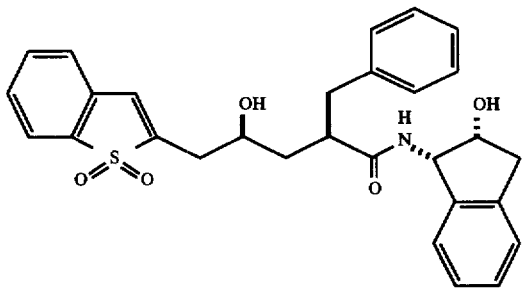

Compound 8b (35 mg, 0.074 mmol) in 1.0 mL of CH$_2$Cl$_2$ was treated with 77 mg (0.223 mmol) of mCPBA (60%) and the whole was stirred for 100 min. The reaction mixture was quenched with 1 mL of sat'd Na$_2$S$_2$O$_3$ and was washed with Et$_2$O (3×5 mL). The combined organic extracts were washed- with sat'd NaHCO$_3$ (3×2 mL), brine then dried (MgSO$_4$). Column chromatography (1:2, EtOAc/Hex) afforded 33 mg (89%) of 8c as a white solid; mp=148°–151° C.).

$^1$H NMR (CDCl$_3$) δ 1.79 (t, J=11.2 Hz, 1H), 2.08 (t, J=10.4 Hz, 1H), 2.70–3.05 (m, 5H), 4.12 (m, 2H), 5.23 (m, 1H), 6.06 (d, J=8.1 Hz, 1H), 6.96 (s, 1H), 7.0–7.4 (m. 12H), 7.77 (d, J=8 Hz, 1H).

IR (CCl$_4$) 3551, 3425, 1643, 1519, 1296, 1148 cm$^{-1}$. MS (FAB) M+1=504.

Anal calc'd for C$_{29}$H$_{29}$NSO$_5$.0.40 H$_2$O: C 68.18; H, 5.88, N, 2.74. Found: C, 68.19; H, 5.95; N, 2.67.

D. Compound 8d

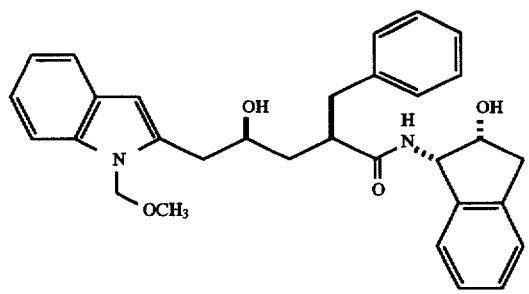

To a 0° C. solution of N-(methoxymethyl) indole (161 mg, 1.0 mmol) in 2 mL of Et$_2$O was added 0.7 mL (1.2 mmol) of t-BuLi (2.5M in pentane). The solution was stirred at this temperature for 10 min before warming to room temperature. After 45 min, the solution was cooled to −70° C. and there resulting anion was then treated with epoxide 3 (125 mg, 0.33 mmol) in 1 mL of THF followed immediately with 0.12 mL (1.0 mmoL) of BF$_3$OEt$_2$. The reaction mixture was stirred for 10 min and quenched with 5 mL of sat'd NaHCO$_3$ and diluted with 5 mL of EtOAc. The aqueous phase was extracted with 3×5 mL of EtOAc. The combined organic extracts were washed with brine and dried over MgSO₄. The yellow oil was subjected to flash chromatography (SiO₂; 1:1 EtOAc/Hex) to afford 113 mg (64%) of acetonide.

The above acetonide (113 mg, 0.21 mmol) in 2 mL of methanol and 1 mL of THF was treated with 146 mg (0.63 mmol) of camphorsulfonic acid and the whole was stirred for 4 h. The solvent was removed with reduced pressure and the residue was taken up in 10 mL of EtOAc and was washed with sat'd NaHCO₃ (3×2 mL). The organic extracts were washed with brine (2×2 mL) and dried (MgSO₄). Column chromatography (1:2, EtOAc/Hex) afforded 95 mg (91%) of 8d as a foam.

¹H NMR (CDCl₃) δ 1.95 (t, J=11.2 Hz, 1H), 2.40 (t, J=10.4 Hz, 1H), 2.60–3.01 (m, 5), 3.25 (s, 3H), 4.01 (t, 1H), 4.18 (m, 1H), 5.25 (m, 1H), 5.40 (ABq, J=8 Hz, 2H), 5.79 (d, J=8.1 Hz, 1H), 7.02 (s, 1H), 7.05–7.5 (m, 13H).

Anal calc'd for C₃₁H₃₄N₂O₄: C, 74.67 H, 6.87, N, 5.62. Found: C, 75.03; H, 6.97; N, 5.72.

E. Compound 8e

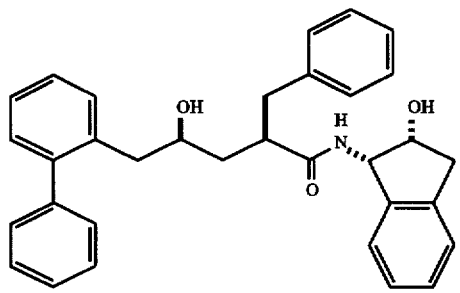

To a –70° C. solution of 2-bromobiphenyl (0.34 mL, 1.99 mmol) in 6 mL of THF was added 0.82 mL (2.05 mmol) of n-BuLi (2.5M in hexanes). The yellow solution was stirred at this temperature for 1 h when the resulting anion was treated with epoxide 3 (250 mg, 0.66 mmol) in 2 mL of THF followed immediately with 0.25 mL (2.05 mmol) of BF₃OEt₂. The reaction mixture was stirred for 20 min and quenched with 5 mL of sat'd NaHCO₃ and diluted with 5 mL of Et₂O.

The aqueous phase was extracted with 3×5 mL of Et₂O. The combined organic extracts were washed with brine and dried over MgSO₄. The resulting oil was used directly without further purification.

The crude acetonide was dissolved in 6 mL of methanol was treated with 232 mg (1.0 mmol) of camphorsulfonic acid and the whole was stirred for 4.25 h. The solvent was removed with reduced pressure and the residue was taken up in 10 mL of EtOAc and was washed with sat'd NaHCO₃ (3×2 mL). The organic extracts were washed with brine (2×2 mL) and dried afforded 8e as a white solid; mp=129°–130° C.).

¹H NMR (CDCl₃) δ 1.58 (t, J=11.2 Hz, 1H), 1.85 (m, 1H), 2.51–3.06 (m, 5H), 3.80 (bs, 1H), 4.20 (bs, 1H), 5.23 (dd, 1H), 5.66 (d, J=8.1 Hz, 1H), 7.0–7.4 (m, 18H).

Anal calc'd for C₃₃H₃₃NO₃.0.25 H₂O: C, 79.88; H, 6.81, N, 2.82. Found: C, 79.58; H, 6.64; N, 2.89.

F. Compound 8f

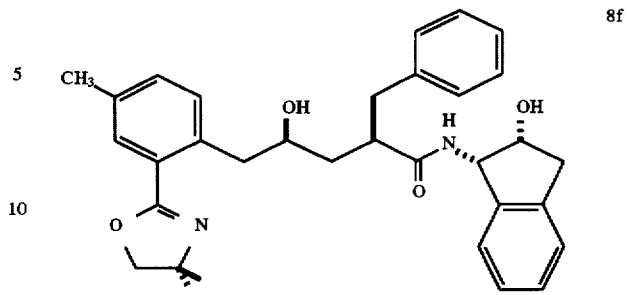

To a –70° C. solution of (2-bromophenyl)-5,5-dimethyl-2-oxazoline (1.52 g, 6.0 mmol) in 10 mL of THF was added 2.4 mL (6.1 mmol) of n-BuLi (2.5M in hexanes). The yellow solution was stirred at this temperature for 40 min when epoxide 3 (755 mg, 2.0 mmol) in 4.2 mL of THF followed by 0.75 mL (6.0 mmol) of BF₃OEt₂ was added. The reaction mixture was stirred for 10 min and quenched with 5 mL of sat'd NaHCO₃ and diluted with 5 mL of Et₂O. The aqueous phase was extracted with 3×5 mL of Et₂O. The combined organic extracts were washed with brine and dried over MgSO₄. The yellow oil was subjected to flash chromatography (SiO₂; 1:4 EtOAc/Hex) to afford 1.06 g (96%) of acetonide.

¹H NMR (CDCl₃) δ 1.20 (s, 3H), 1.30 (s, 3H), 1.40 (s, 3H), 1.64 (s, 3H), 1.84 (m, 1H), 2.00 (m, 1H), 2.80–3.50 (m, 5H), 3.57 (m, 1H), 4.04 (ABq, 2H), 5.99 (d, J=2 Hz, 1H), 6.44 (dd, 1H), 6.99 (t, 1H), 7.2–7.5 (m, 11H), 7.70 (d, J=8 Hz, 1H).

The above acetonide (552 mg, 1.0 mmol) in 5 mL of CH₂Cl₂ and 5 mL of pyridine was treated with excess Ac2O and 12.2 mg (0.1 mmol) of DMAP. The solution was heated at 35° C. for 15 h under nitrogen. The reaction mixture was quenched with sat'd NaHCO₃ (2 mL) and diluted with ether. The organic extract was washed with NaHCO₃ (3×2 mL), H₂O (3×2 mL), and brine (2×2 mL) then dried with MgSO₄. Column chromatography (1:4 EtOAc/Hex) gave material which was used directly in the next step.

¹H NMR (CDCl₃) δ 1.30 (s, 6H), 1.60 (s, 3H), 1.90 (s, 3H), 2.00 (m, 2H), 2.80–3.50 (m, 5H), 4.04 (s, 2H), 4.66 (s, 1H), 4.99 (d, J=2Hz, 1H), 5.29 (m, 1H), 6.11 (d, J=8.1 Hz, 1H), 6.89 (t, 1H), 7.0–7.5 (m, 11H), 7.79 (d, J=8 Hz, 1H).

The above acetonide (260 mg, 0.47 mmol) in 5 mL of methanol was treated with 436 mg (1.88 mmol) of camphorsulfonic acid and the whole was stirred for 1 h. The solvent was removed with reduced pressure and the residue was taken up in 10 mL of EtOAc and was washed with sat'd NaHCO₃ (3×2 mL). The organic extracts were washed with brine (2×2 mL) and dried (MgSO₄). Column chromatography (1:1 EtOAc/Hex) gave material which was used directly in the next step.

¹H NMR (CDCl₃) δ 1.26 (s, 3H), 1.35 (s, 3H), 1.76 (t, J=11.2 Hz, 1H), 2.15 (t, J=10.4 Hz, 1H), 2.50–3.50 (m, 5H), 4.18 (s, 2H), 4.20 (bs, 1H), 5.25 (m, 1H), 5.39 (m, 1H), 6.00 (d, J=8.1 Hz, 1H), 7.0–7.5 (m, 12H), 7.80 (d, J=8 Hz, 1H).

The above acetate (27.7 mg, 0.050 mmol) in 1.0 mL of methanol was treated with 13.8 mg (0.10 mmol) of K₂CO₃ and the whole was stirred at room temperature for 5 h. The solvent was removed with reduced pressure and the residue was taken up in 10 mL of Et₂O and the organic phase was washed with water then brine (2×2 mL) and dried (MgSO₄). Column chromatography (1:1 EtOAc/Hex) afforded 23.1 mg (90%) of 8f mp; 65°–75° C.

¹H NMR (CDCl₃) δ 1.40 (s, 6H), 1.76 (t, J=11.2 Hz, 1H), 2.05 (t, J=10.4 Hz, 1H), 2.80–3.20 (m, 5H), 4.02 (bs, 1H), 4.18 (s, 2H), 4.23 (bs, 1H), 5.29 (m, 1H), 6.10 (d, J=8.1 Hz, 1H), 6.88 (s, 1H), 7.0–7.5 (m, 11 H), 7.80 (d, J=8 Hz, 1H).

Anal calc'd for $C_{32}H_{36}N_2O_4 \cdot 0.50\ H_2O$: C, 73.67; H, 7.15, N, 5.37. Found: C, 73.83; H, 6.97; N, 5.40.

G. Compound 8g

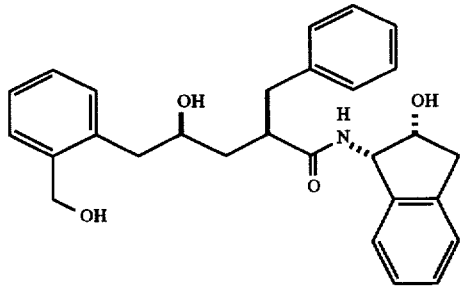

A solution of the oxazoline acetonide of Example 9, Section f, above, (468 mg, 0.847 mmol) was dissolved in 5.3 mL of 2-propanol and cooled to 0° C. The solution was treated with 2.65 mL of 8N HCl and was allowed to stir to ambient temperature over 2.5 h. The resulting white precipitate which formed was filtered to give 233 mg (62%) of lactone.

$^1$H NMR (CDCl$_3$) δ 2.00 (t, 1H), 2.30 (t, 1H), 2.80–3.09 (m, 5H), 4.10 (t, 1H), 4.60 (dt, 1H), 5.21 (dd, 1H), 5.95 (d, J=7Hz, 1H), 6.9–7.6 (m, 12H), 8.1 (d, J=8 Hz, 1H).

The above lactone (220 mg, 0.50 mmol) was dissolved in 10 mL of EtOH, 5 mL of CH$_2$Cl$_2$ and 2.5 mL of H$_2$O and treated with 220 mg (5.8 mmol) of NaBH$_4$ and the whole was stirred for 1.5 h. The reaction mixture was quenched with 10 mL of EtOAc and was washed with sat'd NH$_4$Cl (3×2 mL). The organic extracts were washed with brine (2×2 mL) and dried (MgSO$_4$). The residue left after evaporation was recrystallized from MeOH and Et$_2$O to afford 180 mg (81%) of 8g as a white solid; mp=160°–161° C.).

$^1$H NMR (CDCl$_3$) δ 1.86 (t, J=10.2 Hz, 1H), 2.08 (t, J=10.4 Hz, 1H), 2.70–3.01 (m, 5H), 4.04 (bt, 1H), 4.21 (m, 1H), 4.54 (d, J=14 Hz, 1H), 4.79 (d, J=14 Hz, 1H), 5.23 (m, 1H), 5.96 (d, J=8.1 Hz, 1H), 7.0–7.4 (m, 13H). MS (FAB) M+1=546.

Anal calc'd for $C_{28}H_{31}NO_4 \cdot 0.50\ H_2O$: C, 73.98; H, 7.10, N, 3.08. Found: C, 73.89; H, 6.82; N, 3.12.

H. Compound 8h

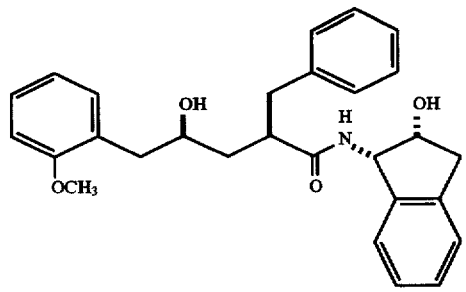

To a 0° C. solution of 2-bromoanisole (0.37 mg, 3.0 mmol) in 10 mL of Et$_2$O was added 1.2 mL (3.0 mmol) of n-BuLi (2.5M in hexanes). The yellow solution of 2-lithioanisole precipitates and the slurry was stirred at this temperature for 1 h before cooling to –70° C. The resulting anion was treated with epoxide 3 (377.5 mg, 1.0 mmol) in 3 mL of THF followed immediately with 0.35 mL (3.1 mmoL) of BF$_3$OEt$_2$. The reaction mixture was stirred for 10 min and quenched with 4 mL of sat'd NaHCO$_3$ and diluted with 5 mL of Et$_2$O. The aqueous phase was extracted with 3×5 mL of Et$_2$O. The combined organic extracts were washed with brine and dried over MgSO$_4$. The yellow oil was subjected to flash chromatography (SiO$_2$; gradient 1:4, 1:1 EtOAc/Hex) to afford 200 mg (41.5%) of acetonide.

The above acetonide (200 mg, 0.415 mmol) was dissolved in 8 mL of 2-propanol and cooled to 0° C. The solution was treated with 1.3 mL of 8N HCl and was allowed to stir to ambient temperature over 3 h. The pH of the solution was then adjusted to 9 by the dropwise addition of 50% NaOH at 0° C. The aqueous solution was extracted with 3×5 mL portions of CH$_2$Cl$_2$ and the combined organic extracts were washed with brine (2×5 mL) and dried (MgSO$_4$). Column chromatography (7:3 EtOAc/Hex) afforded 385 mg (87%) of 8h as a white solid; mp=140°–142° C.).

$^1$H NMR (CDCl$_3$) δ 1.66 (t, J=10.2 Hz, 1H), 2.08 (t, J=10.4 Hz, 1H), 2.70–3.01 (m, 5H), 3.80 (s, 3H), 4.04 (bt, 1H), 4.21 (m, 1H), 5.26 (m, 1H), 5.80 (d, J=8.1 Hz, 1H), 6.80–7.40 (m, 13H). MS (FAB) M+1=446.

Anal calc'd for $C_{28}H_{31}NO_4 \cdot 0.25\ H_2O$: C, 74.72; H, 7.05, N, 3.11. Found: C, 74.43; H, 6.90; N, 3.31.

I. Compound 8i

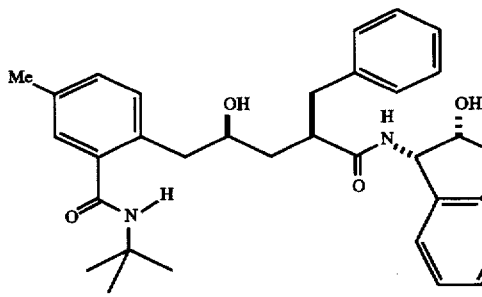

To a –70° C. solution of 2,5-Dimethyl-N-tert-butylbenzamide (410 mg, 2.0 mmol) in 10 mL of THF was added 0.6 mL (4.0 mmol) of TMEDA and 3.0 mL (4.0 mmol) of sec-BuLi (1.3M in cyclohexane). The red solution was stirred at this temperature for 15 min before warming to –15° C. After stirring at this temperature for 30 min, 181.5 mg (0.50 mmol) of aldehyde J in 2 mL of THF was added. The reaction mixture was stirred for 25 min and quenched with 5 mL of H$_2$O and diluted with 5 mL of Et$_2$O. The aqueous phase was extracted with 3×5 mL of Et$_2$O. The combined organic extracts were washed with brine and dried over MgSO$_4$. The yellow oil was subjected to flash chromatography (SiO$_2$; gradient: 1:2, 1:1 EtOAc/Hex) to afford 213 mg (75%) of acetonide.

The acetonide (28.4 mg, 0.05 mmol) was dissolved in 2 mL of MeOH and was treated with 36.3 mg (0.15 mmol) of camphorsulfonic acid and the whole was stirred for 3 h. The solvent was removed with reduced pressure and the residue was taken up in 10 mL of EtOAc and was washed with sat'd NaHCO$_3$ (3×2 mL). The organic extracts were washed with brine (2×2 mL) and dried (MgSO$_4$). Column chromatography (gradient; 1:2, 1:1 EtOAc/Hex) afforded 25 mg (98%) of 8i as a white solid; mp=99°–109° C.).

$^1$H NMR (CDCl$_3$) δ 1.40 (s, 9H), 1.76 (t, J=11.2 Hz, 1H), 2.10 (t, J=10.4 Hz, 1H), 2.35 (s, 3H), 2.70–3.01 (m, 5H), 3.88 (bs, 1H), 4.16 (m, 1H), 5.21 (dd, J=5.1, 6.9 Hz, 1H), 5.45 (d, J=5.1 Hz, 1H), 6.02 (m, 2H), 7.0–7.4 (m, 12H).

Anal calc'd for $C_{33}H_{40}N_2O_3 \cdot 1.5\ H_2O$: C, 71.32; H, 7.80, N, 5.04. Found: C, 71.05; H, 7.41; N, 5.08.

J. Compound 8j

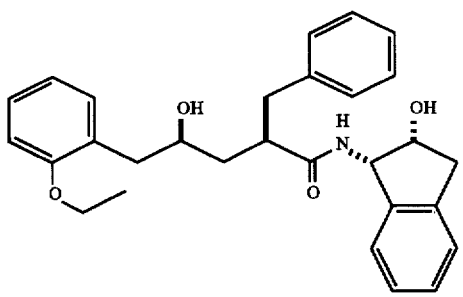

To a 0° C. solution of 2-ethoxybromobenzene (400 mg, 1.98 mmol) in 6.6 mL of $Et_2O$ was added 0.79 mL (1.98 mmol) of n-BuLi (2.5M in hexanes). The yellow solution was stirred at this temperature for 1 h before cooling to −70° C. The resulting dianion was then treated with epoxide 3 (250 mg, 0.66 mmol) in 2 mL of THF followed immediately with 0.24 mL (1.98 mmoL) of $BF_3OEt_2$. The reaction mixture was stirred for 30 min, quenched with sat'd $NaHCO_3$ and diluted with EtOAc. The organic extract was washed with water and brine and dried over $Na_2SO_4$. The yellow oil was subjected to flash chromatography ($SiO_2$; 15:85 EtOAc/Hex) to afford 230 mg (70%) of acetonide.

The above acetonide (180 mg, 0.36 mmol) in 7.2 ml of methanol was treated with camphorsulfonic acid (230 mg, 0.97 mmol) and the whole was stirred for 2 h. The solvent was removed with reduced pressure, the residue taken up in EtOAc and washed with sat'd $NaHCO_3 \times 2$. The organic extract was washed with brine and dried over $Na_2SO_4$. Column chromatography ($SiO_2$; 35% EtOAc/Hex) and trituration with EtOAc/Hex afforded 68 mg (42%) of 8j as a white solid; mp=117°–119° C.

$^1$H NMR ($CDCl_3$) δ 0.85 (d, 1H), 1.43 (t, 3H, J=6.8 Hz), 1.70 (t, 1H), 2.09 (t, 1H), 2.66 (d, 1H), 2.82 (m, 4H), 3.00 (m, 3H), 4.08 (m, 3H), 4.23 (m, 1H), 5.29 (m, 1H), 5.76 (d, J=8.4 Hz, 1H), 6.88–7.33 (m, 13H).

Anal calc'd for $C_{29}H_{33}NO_4$: C, 75.78; H, 7.25, N, 3.05. Found: C, 75.66; H, 7.21; N, 3.17.

K. Compound 8k

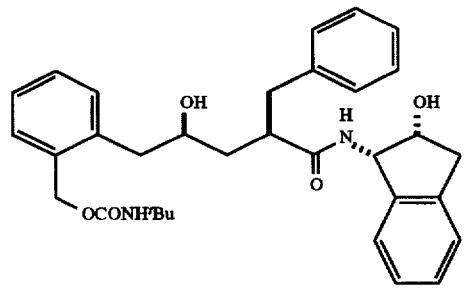

To a solution of 8g (75 mg, 0.17 mmol) and copper(I) chloride (16.8 mg, 0.17 mmol) in 1 ml of DMF was added tert-butyl isocyanate (20 ml, 0.17 mmol). The reaction was stirred at ambient temperature for 2 h and tert -butyl isocyanate (10 ml) and copper(I) chloride (8 mg) were added. After stirring an additional 4 h, the reaction mixture was diluted with EtOAc, washed with water and brine and dried over $Na_2SO_4$. Column chromatography ($SiO_2$; 55% EtOAc/ Hex) afforded 31 mg (33%) of 8k as a white solid; mp=144°–147° C.

$^1$H NMR ($CDCl_3$) δ 1.20 (s, 9H), 1.72 (t, 1H), 2.01 (t, 1H), 2.82 (m, 5H), 3.05 (m, 3H), 3.44 (bs, 1H), 3;.70 (bs, 1H), 4.04 (bs, 1H), 4.38 (m, 1H), 4.63 (m, 2H), 5.18 (bs, 1H), 5.51 (m, 1H), 6.08 (d, 1H), 7.03–7.36 (m, 13H).

L. Compound 8l

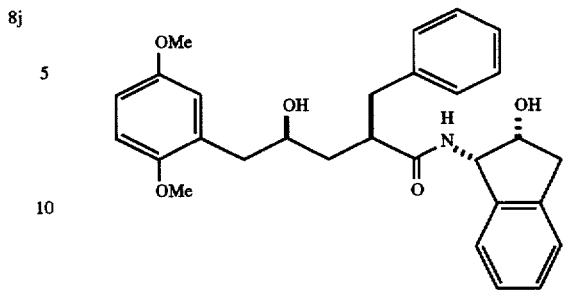

To a 0° C. solution of 1-bromo-2,5-dimethoxybenzene (0.30 ml, 1.98 mmol) in 6.6 mL of $Et_2O$ was added 0.79 mL (1.98 mmol) of n-BuLi (2.5M in hexanes). The yellow solution was stirred at this temperature for 1 h before cooling to −70° C. The resulting dianion was then treated with epoxide 3 (250 mg, 0.66 mmol) in 2 mL of THF followed immediately with 0.24 mL (1.98 mmoL) of $BF_3OEt_2$. The reaction mixture was stirred for 45 min, quenched with sat'd $NaHCO_3$ and diluted with EtOAc. The organic extract was washed with water and brine and dried over $Na_2SO_4$. The yellow oil was subjected to flash chromatography ($SiO_2$; 1:4 EtOAc/Hex) to afford 260 mg (76%) of acetonide.

The above acetonide (260 mg, 0.50 mmol) in 10 ml of methanol was treated with camphorsulfonic acid (310 mg, 1.35 mmol) and the whole was stirred for 3 h. The solvent was removed with reduced pressure, the residue taken up in EtOAc and washed with sat'd $NaHCO_3 \times 2$. The organic extract was washed with brine and dried over $Na_2SO_4$. Column chromatography ($SiO_2$; 2:3 EtOAc/Hex) and trituration with EtOAc/Hex afforded 89 mg (37%) of 81 as a white solid; mp=148°–150° C.

$^1$H NMR ($CDCl_3$) δ 0.89 (d, 1H), 1.70 (t, 1H), 2.08 (t, 1H), 2.61 (d, 1H), 2.79 (m, 4H), 2.95 (m, 3H), 3.76 (s, 3H), 3.80 (s, 3H), 4.04 (m, 1H), 4.22 (m, 1H), 5.29 (m, 1H), 5.78 (d, 1H), 6.75 (m, 2H), 6.82 (m, 1H), 7.03–7.31 (m, 9H).

M. Compound 8m

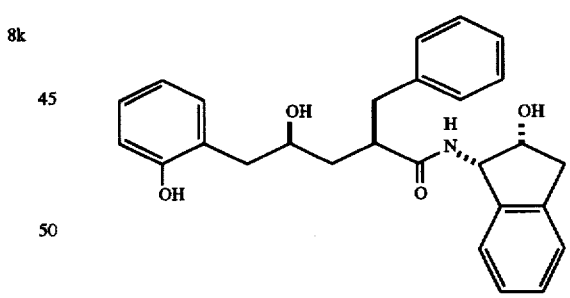

To a −70° C. solution of the acetonide of Example 9, Section H, above (500 mg, 1.0 mmol) in 10 mL of $CH_2Cl_2$ was added dropwise 1.4 ml (1.4 mmol) of $BBr_3$ (1.0M in $CH_2Cl_2$). The reaction was allowed to stir to ambient temperature overnight, quenched with cold water and stirred for 30 minutes. The aqueous phase was extracted with $CH_2Cl_2 \times 2$ and the combined organic extracts were dried over $Na_2SO_4$. Column chromatography ($SiO_2$; 35% EtOAc/ Hex) and recrystallization from EtOAc/Hex afforded 240 mg (56%) of 8m as a white solid; mp=186°–188° C.

$^1$H NMR ($CDCl_3$) δ 0.71 (d, 1H), 1.94 (m, 2H), 2.80 (m, 4H), 2.91 (m, 1H), 3.04 (m, 3H), 4.18 (m, 1H), 4.41 (m, 1H), 5.23 (m, 1H), 5.79 (d, J=6.4 Hz, 4H), 6.06 (bs, 3H), 6.82–7.;37 (m, 13H), 8.90 (s, 3H).

N. Compound 8n

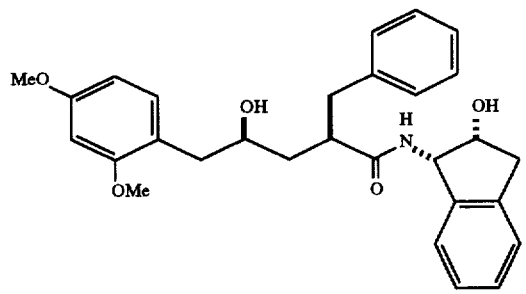

To a 0° C. solution of 1-bromo-2,4-dimethoxybenzene (0.28 ml, 1.98 mmol) in 6.6 mL of $Et_2O$ was added 0.79 mL (1.98 mmol) of n-BuLi (2.5M in hexanes). The yellow solution was stirred at this temperature for 1 h before cooling to −70° C. The resulting dianion was then treated with epoxide 3 (250 mg, 0.66 mmol) in 2 mL of THF followed immediately with 0.24 mL (1.98 mmoL) of $BF_3OEt_2$. The reaction mixture was stirred for 1 h, quenched with sat'd $NaHCO_3$ and diluted with EtOAc. The organic extract was washed with water and brine and dried over $Na_2SO_4$. The yellow oil was subjected to flash chromatography ($SiO_2$; 1:4 EtOAc/Hex) to afford 0.27 g (79%) of acetonide.

The above acetonide (270 mg, 0.52 mmol) in 10 ml of methanol was treated with camphorsulfonic acid (330 mg, 1.4 mmol) and the whole was stirred for 6 h. The solvent was removed with reduced pressure, the residue taken up in EtOAc and washed with sat'd $NaHCO_3×2$. The organic extract was washed with brine and dried over $Na_2SO_4$. Column chromatography ($SiO_2$; 2:3 EtOAc/Hex) and recrystallization from EtOAc/Hex afforded 66 mg (26%) of 8n as a white solid; mp=184°–186° C.

$^1$H NMR ($CDCl_3$) δ 0.87 (d, 1H), 1.68 (t, 1H), 2.08 (t, 1H), 2.40 (d, 1H), 2.67–3.01 (m, 7H), 3.82 (s, 6H), 4.00 (m, 1H), 4.24 (m, 1H), 5.30 (m, 1H), 5.77 (d, J=8.8 Hz, 1H), 6.50 (m, 2H), 7.04–7.33 (m, 10H).

Anal calc'd for $C_{29}H_{33}NO_5$: C, 73.23; H, 7.01, N, 2.94. Found: C, 73.11; H, 6.92; N, 3.00.

P. Compound 8p

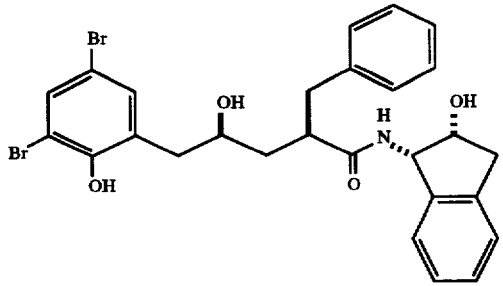

To a solution of tert-butylamine (0.49 ml, 0.46 mmol) in 0.6 ml of toluene, cooled to −25° C., was added 0.46 ml (0.23 mmol) bromine (0.5M in $CH_2Cl_2$). The mixture was cooled to −70° C. and 8m (100 mg, 0.23 mmol) was added. The reaction was stirred at ambient temperature for 2 h and diluted with $CH_2Cl_2$. The organic phase was washed with water and dried over $Na_2SO_4$. Column chromatography ($SiO_2$; 35% EtOAc/Hex) and recrystallization from EtOAc/Hex afforded 20 mg (14%) of 8p as a white solid; mp=197°–199° C.

$^1$H NMR ($CDCl_3$) δ 0.72 (d, 1H), 1.90 (m, 2H), 2.92 (m, 7H), 4.19 (m, 1H), 4.41 (bs, 1H), 5.23 (m, 1H), 5.83 (d, J=8.4 Hz, 1H), 6.44 (s, 1H), 7.12–7.38 (m, 10H), 7.55 (s, 1H), 9.53 (s, 1H).

Anal calc'd for $C_{27}H_{27}Br_2NO_4$: C, 55.02; H, 4.63, N, 2.38. Found: C, 54.79; H, 4.69; N, 2.37.

Q. Compound 8q

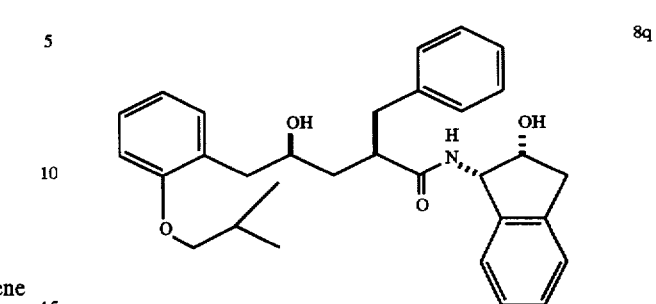

To a 0° C. solution of 2-isobutoxybromobenzene (300 g, 1.32 mmol) in 4.4 mL of $Et_2O$ was added 0.53 mL (1.32 mmol) of n-BuLi (2.5M in hexanes). The yellow solution was stirred at this temperature for 1 h before cooling to −70° C. The resulting dianion was then treated with epoxide 3 (250 g, 0.66 mmol) in 2 mL of THF followed immediately with 0.16 mL (1.32 mmoL) of $BF_3OEt_2$. The reaction mixture was stirred for 1 h, quenched with sat'd $NaHCO_3$ and diluted with EtOAc. The organic extract was washed with water and brine and dried over $Na_2SO_4$. The yellow oil was subjected to flash chromatography ($SiO_2$; 15% EtOAc/Hex) to afford 83 mg (24%) of acetonide.

The above acetonide (83 mg, 0.16 mmol) in 3 ml of methanol was treated with camphorsulfonic acid (100 mg, 0.43 mmol) and the whole was stirred for 6 h. The solvent was removed with reduced pressure, the residue taken up in EtOAc and washed with sat'd $NaHCO_3×2$. The organic extract was washed with brine and dried over $Na_2SO_4$. Column chromatography ($SiO_2$; 30% EtOAc/Hex) and trituration with EtOAc/Hex afforded 24 mg (31%) of 8q as a white solid; mp=107°–108° C.

$^1$H NMR ($CDCl_3$) δ 0.81 (d, 1H), 1.04 (d, J=6.4 Hz, 6H), 1.71 (t, 1H), 2.10 (m, 2H), 2.54 (m, 1H), 2.89 (m, 7H), 3.76 (d, J=6.4 Hz, 2H), 4.07 (m, 1H), 4.22 (m, 1H), 5.27 (m, 1H), 5.74 (d, J=8.4 Hz, 1H), 6.88–7.32 (m, 13H).

R. Compound 8r

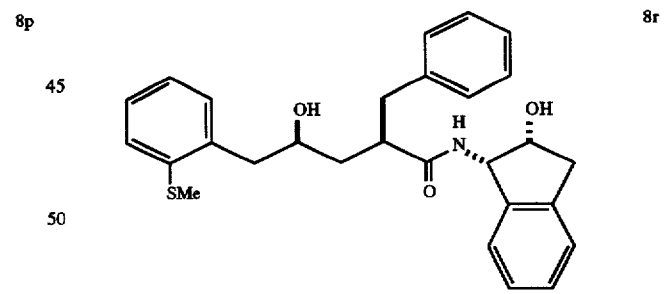

To a 0° C. solution of 2-bromothioanisole (0.26 ml, 1.98 mmol) in 6.6 mL of $Et_2O$ was added 0.79 mL (1.98 mmol) of n-BuLi (2.5M in hexanes). The yellow solution was stirred at this temperature for 1 h before cooling to −70° C. The resulting dianion was then treated with epoxide 3 (250 g, 0.66 mmol) in 2 mL of THF followed immediately with 0.24 mL (1.98 mmoL) of $BF_3OEt_2$. The reaction mixture was stirred for 30 min, quenched with sat'd $NaHCO_3$ and diluted with EtOAc. The organic extract was washed with water and brine and dried over $Na_2SO_4$. The yellow oil was subjected to flash chromatography ($SiO_2$; 20% EtOAc/Hex) to afford 0.26 g (79%) of acetonide.

The above acetonide (260 mg, 0.52 mmol) in 10 ml of methanol was treated with camphorsulfonic acid (320 mg, 1.4 mmol) and the whole was stirred for 4 h. The solvent was removed with reduced pressure, the residue taken up in EtOAc and washed with sat'd NaHCO₃×2. The organic extract was washed with brine and dried over Na₂SO₄. Column chromatography (SiO₂; 2:3 EtOAc/Hex) and trituration with EtOAc/Hex afforded 71 mg (30%) of 8r as a white solid; mp=139°–141° C.

¹H NMR (CDCl₃) δ 0.90 (d, 1H), 1.78 (t, 1H), 2.16 (m, 2H), 2.47 (s, 3H), 2.78–3.06 (m, 8H), 4.15 (m, 1H), 4.24 (m, 1H), 5.30 (m, 1H), 5.78 (d, 1H), 7.08–7.35 (m, 13H).

S. Compound 8s

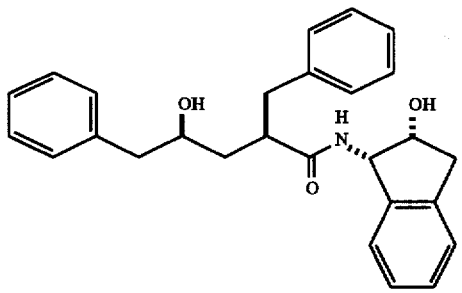

To a solution of phenyllithium (1.1 ml, 1.98 mmol, 1.8M in cyclohexane-ether) in 5 ml of THF, cooled to −70° C., was added dropwise a solution of epoxide 3 (250 mg, 0.66 mmol). BF₃OEt₂ (0.24 ml, 1.98 mmol) was added and the whole was stirred at −70° C. for 1 h. The reaction was quenched with sat'd NaHCO₃ and diluted with EtOAc. The organic phase was washed with water and brine, dried over Na₂SO₄ and concentrated under reduced pressure to afford 300 mg (100%) of acetonide 7 of Example 9.

A solution of acetonide 7 (300 mg, 0.66 mmol) and p-toluenesulfonic acid (380 mg, 2.0 mmol) in 5 ml of benzene was stirred at ambient temperature for 1 h. The reaction mixture was diluted with EtOAc, washed with sat'd NaHCO₃×2, water and brine and dried over Na₂SO₄. Column chromatography (SiO₂, 35% EtOAc/Hex) and trituration with EtOAc/Hex afforded 93 mg (34%) of 8s as a white solid; mp=160°–162° C.

¹H NMR (CDCl₃) δ 0.80 (d, 1H), 1.73 (t, 1H), 2.00 (s, 1H), 2.15 (t, 1H), 2.69–3.05 (m, 7H), 4.02 (bs, 1H), 4.22 (m, 1H), 5.30 (m, 1H), 5.75 (d, J=8 Hz, 1H), 7.01–7.37 (m, 14H).

T. Compound 8t

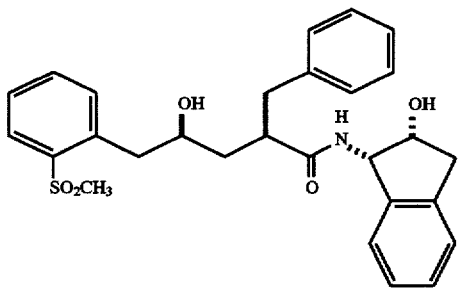

A solution of 8r (59 mg, 0.13 mmol) and potassium peroxymonosulfate (0.12g, 0.2 mmol) in 6 ml of ethanol and 2.6 ml of water was stirred at ambient temperature overnight. The reaction mixture was quenched with sat'd NaHCO₃ and diluted with EtOAc. The organic phase was washed with water×2, brine and dried over Na₂SO₄. Column chromatography (SiO₂; 3:2 EtOAc/Hex) and trituration with EtOAc/Hex afforded 50 mg (78%) of 8t as a white solid; mp=155°–157° C.

¹H NMR (CDCl₃) δ 1.06 (bs, 1H), 1.81 (t, 1H), 2.16 (t, 1H), 2.78–3.29 (m, 8H), 3.11 (s, 3H), 4.04 (m, 1H), 4.24 (m, 1H), 5.27 (m, 1H), 5.84 (d, J=8.4 Hz, 1H), 7.01–7.63 (m, 12H), 8.07 (d, J=8 Hz, 1H).

Anal calc'd for C₂₈H₃₁NO₅S: C, 68.12; H, 6.34, N, 2.84. Found: C, 68.08; H, 6.27; N, 3.05.

U. Compound 8u

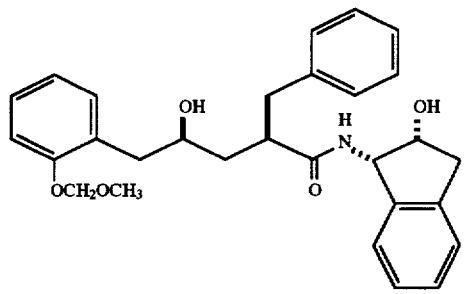

To a 0° C. solution of 2-(methoxymethoxy)-bromobenzene (430 mg, 1.98 mmol) in 6.6 mL of Et₂O was added 0.79 mL (1.98 mmol) of n-BuLi (2.5M in hexanes). The yellow solution was stirred at this temperature for 1 h before cooling to −70° C. The resulting dianion was then treated with epoxide 3 (250 mg, 0.66 mmol) in 2 mL of THF followed immediately with 0.24 mL (1.98 mmoL) of BF₃OEt₂. The reaction mixture was stirred for 2 hrs, quenched with sat'd NaHCO₃ and diluted with EtOAc. The organic extract was washed with water and brine and dried over Na₂SO₄. The yellow oil was subjected to flash chromatography (SiO₂; 1:5 EtOAc/Hex) to afford 61 mg (18%) of acetonide.

The above acetonide (61 mg, 0.12 mmol) was dissolved in 30 ml acetic acid solution (60% in water) and allowed to stir at ambient temperature for 7 days. The reaction mixture was diluted with water, neutralized with NaHCO₃ and extracted with EtOAc×3. The combined organic extracts were washed with brine and dried over Na₂SO₄. Column chromatography (SiO₂; 2:3 EtOAc/Hex) afforded 18 mg (32%) of 8u as a white solid; mp=115°–117° C.

¹H NMR (CDCl₃) δ 0.87 (bs, 1H), 1.73 (t, 1H), 2.11 (t, 1H), 2.82 (m, 5H), 2.97 (m, 3H), 3.47 (s, 3H), 4.07 (m, 1H), 4.23 (m, 1H), 5.20 (s, 2H), 5.27 (m, 1H), 5.78 (d, 1H), 6.98–7.34 (m, 13H).

V. Compound 8v

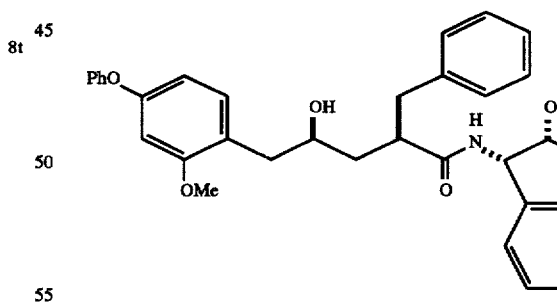

To a 0° C. solution of 2-methoxy-4-phenoxybromobenzene (360 mg, 1.3 mmol) in 4.3 mL of Et₂O was added 0.52 mL (1.3 mmol) of n-BuLi (2.5M in hexanes). The yellow solution was stirred at this temperature for 1 h before cooling to −70° C. The resulting dianion was then treated with epoxide 3 (250 mg, 0.66 mmol) in 2 mL of THF followed immediately with 0.16 mL (1.3 mmoL) of BF₃OEt₂. The reaction mixture was stirred for 45 min, quenched with sat'd NaHCO₃ and diluted with EtOAc. The organic extract was washed with water and brine and dried over Na₂SO₄. The crude acetonide product was taken on to the next reaction.

The above acetonide (380 mg, 0.66 mmol) in 13 ml of methanol was treated with camphorsulfonic acid (420 mg, 1.8 mmol) and the whole was stirred for 6 h. The solvent was removed with reduced pressure, the residue taken up in EtOAc and washed with sat'd NaHCO$_3$×2. The organic extract was washed with brine and dried over Na$_2$SO$_4$. Column chromatography (SiO$_2$; 2:3 EtOAc/Hex) and recrystallization from EtOAc/Hex afforded 80 mg (23%) of 8v as a white solid; mp=175°–177° C.

$^1$H NMR (CDCl$_3$) δ 0.90 (d, 1H), 1.70 (t, 1H), 2.10 (t, 1H), 2.40 (d, 1H), 2.71–3.01 (m, 7H), 3.79 (s, 3H), 4.03 (m, 1H), 4.24 (m, 1H), 5.30 (m, 1H), 5.79 (d, J=8.4 Hz, 1H), 6.54 (dd, 1H, J=2.0, 8.0 Hz, 1H), 6.63 (d, J=2 Hz, 1H), 7.02–7.37 (m, 15H).

Anal calc'd for C$_{34}$H$_{35}$NO$_5$: C, 75.94 H, 6.57, N, 2.60. Found: C, 75.69; H, 6.54; N, 2.65.

EXAMPLE 10

A. 2-Ethoxybromobenzene

To a solution of 2-bromophenol (1.3 ml, 0.012 mol) in 50 ml acetone was added K$_2$CO$_3$ (4.1 g, 0.03 mol) and iodoethane (1.0 ml, 0.013 mol). The reaction mixture was heated to reflux for 8 h, cooled to ambient temperature and filtered. The solvent was removed under reduced pressure and the residue was taken up in EtOAc. The organic phase was washed with 1N NaOH×2, water and brine. Drying over Na$_2$SO$_4$ afforded 2.1 g (88%) of 2-ethoxybromobenzene.

$^1$H NMR (CDCl$_3$) δ 1.48 (t, 3H), 4.09 (q, 2H), 6.80 (t, 1H), 6.88 (d, 1H), 7.23 (m, 1H), 7.52 (d, 1H).

B. 2-Isobutoxybromobenzene

To a solution of 2-bromophenol (0.67 ml, 5.8 mmol) in 25 ml acetone was added K$_2$CO$_3$ (2.0 g, 14.5 mmol) and 1-iodo-2-methylpropane (0.75 ml, 6.4 mmol). The reaction mixture was heated to reflux for 19 h, cooled to ambient temperature and filtered. The solvent was removed under reduced pressure and the residue was taken up in EtOAc. The organic phase was washed with 1N NaOH×2, water and brine. Drying over Na$_2$SO$_4$ afforded 330 mg (25%) of 2-isobutoxybromobenzene.

1H NMR (CDCl$_3$) δ 1.09 (d, 6H), 2.17 (m, 1H), 3.78 (d, 2H), 6.80 (t, 1H), 6.87 (d, 1H), 7.22 (t, 1H), 7.52 (d, 1H).

C. 2-(Methoxymethoxy)-bromobenzene

To a solution of 2-bromophenol (0.67 ml, 5.8 mmol) and diisopropylethylamine (1.1 ml, 6.4 mmol) was added chloromethyl methyl ether (0.49 ml, 6.4 mmol). The reaction mixture was stirred at ambient temperature for 2 h, quenched with sat'd NaHCO$_3$ and diluted with CH$_2$Cl$_2$. The organic phase was washed with water and dried over Na$_2$SO$_4$ to afford 700 mg (58%) of the title compound.

$^1$H NMR (CDCl$_3$) δ 3.52 (s, 3H), 5.24 (s, 2H), 6.88 (t, 1H), 7.15 (d, 1H), 7.25 (m, 1H), 7.54 (d, 1H).

D. 2-Bromo-5-phenoxyphenol

To a solution of t-butylamine (1.1 ml, 10.7 mmol) in 13 ml toluene, cooled to −30° C. was added bromine (0.28 ml, 5.35 mmol). The mixture was cooled to −70° C. and was treated with 3-phenoxyphenol (2.0 g, 10.7 mmol) dissolved in 2 ml CH$_2$Cl$_2$. The reaction was stirred to ambient temperature over 5 h, quenched with water and diluted with CH$_2$Cl$_2$. The organic phase was washed with water and brine and dried over Na$_2$SO$_4$. Column chromatography (SiO$_2$; 5:95 EtOAc/Hex) afforded 380 mg (14%) of 2-bromo-5-phenoxyphenol.

$^1$H NMR (CDCl$_3$) δ 5.48 (s, 1H), 6.49 (dd, 1H), 6.67 (d, 1H), 7.01 (d, 2H), 7.13 (t, 1H), 7.35 (m, 3H).

E. 2-Methoxy-4-phenoxybromobenzene

To a solution of 2-bromo-5-phenoxyphenol (0.38 g, 1.4 mmol) in 6 ml acetone was added K$_2$CO$_3$ (0.58 g, 4.2 mmol) and iodomethane (0.26 ml, 4.2 mmol). The reaction mixture was heated to reflux for 8 h, cooled to ambient temperature and filtered. The solvent was removed under reduced pressure and the residue was taken up in EtOAc. The organic phase was washed with 1N NaOH, water and brine. Drying over Na$_2$SO$_4$ afforded 0.36 g (92%) of 2-methoxy-4-phenoxybromobenzene.

$^1$H NMR (CDCl$_3$) δ 3.83 (s, 3H), 6.45 (dd, 1H), 6.62 (d, 1H), 7.00 (d, 2H), 7.12 (t, 1H), 7.34 (t, 2H), 7.43 (d, 1H).

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A compound of the formula

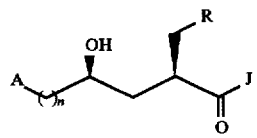

Wherein

A is
  1) aryl unsubstituted or substituted with one or more of
     a) $C_{1-4}$ lower alkyl;
     b) hydroxy;
     c) halo;
     d) $C_{1-4}$ lower or branched alkoxy;
     e) $C_{1-4}$ lower branched thioalkyl;
     f) COOR$^1$;
     g) CONHR$^1$;
     h) SO$_2$NHR$^1$;
     i) SO$_2$R$^1$; or
     j) $C_{1-4}$ lower hydroxyalkyl; or
  2) a 5- to 10-membered mono or bicyclic heterocycle in which one or both heterocyclic rings contain an atom selected from N, O, or S, which heterocycle is unsubstituted or substituted with one or more of
     a) $C_{1-4}$ lower alkyl;
     b) hydroxy;
     c) halo;
     d) $C_{1-4}$ lower or branched alkoxy;
     e) $C_{1-4}$ lower branched thioalkyl;
     f) COOR$^1$;
     g) CONHR$^1$;
     h) SO$_2$NHR$^1$;
     i) SO$_2$R$^1$; or
     j) $C_{1-4}$ lower hydroxyalkyl; and R is
  1) aryl, unsubstituted or substituted with $C_{1-4}$ lower alkyl, $C_{1-4}$ lower alkoxy, or halo, or
  2) $C_{3-7}$ cycloalkyl; and R$^1$ is $C_{1-4}$ lower alkyl, $C_{3-7}$ cycloalkyl or H; and J is:

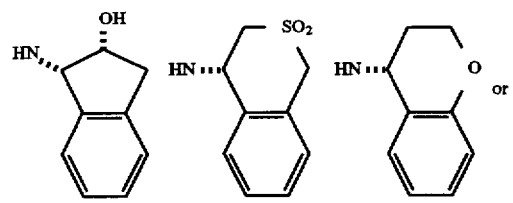

-continued

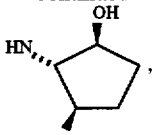

or pharmaceutically acceptable salt(s) thereof.

2. A compound according to claim 1, of the formula:

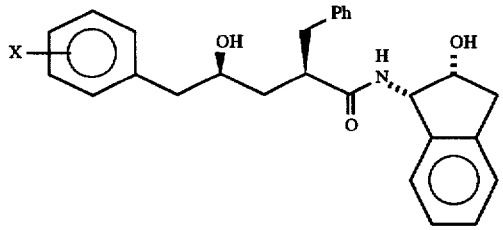  II

X is COOR¹; CONHR¹; SO₂NHR¹, or SO₂R¹;
or a pharmaceutically acceptable salt thereof.

3. A compound according to claim 1, of the formula

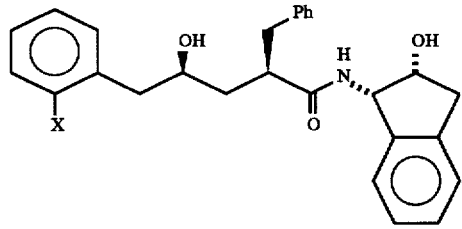  III

X is CONHR¹ or SO₂NHR¹,
or pharmaceutically acceptable salt thereof.

4. The compound, which is

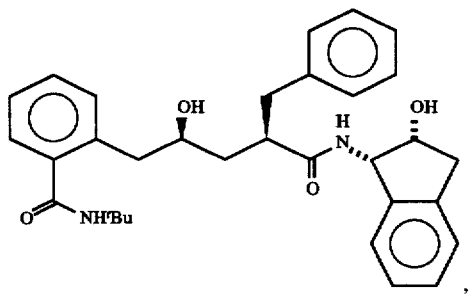

or pharmaceutically acceptable salts thereof.

5. The compound, which is

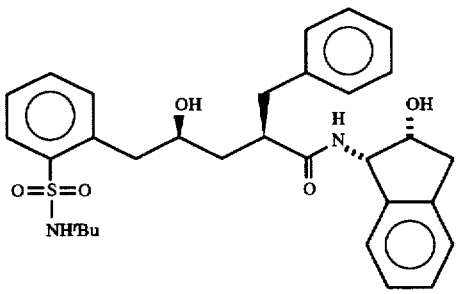

or pharmaceutically acceptable salts thereof.

6. The compound, which is

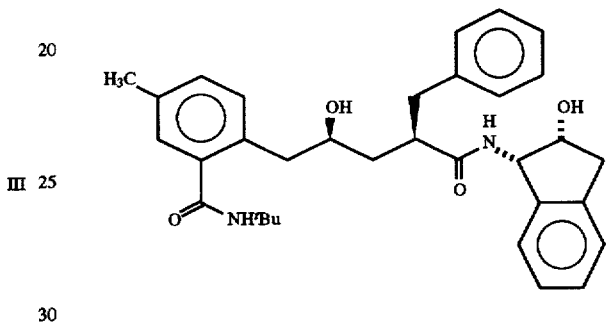

or pharmaceutically acceptable salts thereof.

7. A pharmaceutical composition comprising the compound of any of claims 1–6 and a pharmaceutically acceptable carrier.

8. A method of treating and delaying the onset of AIDS, comprising administering to a mammal in need of such treatment an effective amount of a compound of any of claims 1–6.

9. A method of treating infection by HIV, comprising administering to a mammal in need of such treatment an effective amount of a compound of any of claims 1–6.

10. A method of inhibiting HIV protease, comprising administering to a mammal in need of such treatment an effective amount of a compound of any of claims 1–6.

11. A composition comprising the compound of claim 6, and any of AZT or ddI or ddC.

* * * * *